US011730952B2

(12) United States Patent
Song et al.

(10) Patent No.: US 11,730,952 B2
(45) Date of Patent: Aug. 22, 2023

(54) APPARATUS AND METHOD FOR DECODING AND RESTORING COGNITIVE FUNCTIONS

(71) Applicant: University of Southern California, Los Angeles, CA (US)

(72) Inventors: Dong Song, Walnut, CA (US); Theodore William Berger, Rancho Palos Verdes, CA (US)

(73) Assignee: University of Southern California, Los Angeles, CA (US)

( * ) Notice: Subject to any disclaimer, the term of this patent is extended or adjusted under 35 U.S.C. 154(b) by 490 days.

(21) Appl. No.: 16/639,556

(22) PCT Filed: Aug. 16, 2018

(86) PCT No.: PCT/US2018/000151
§ 371 (c)(1),
(2) Date: Feb. 14, 2020

(87) PCT Pub. No.: WO2019/035887
PCT Pub. Date: Feb. 21, 2019

(65) Prior Publication Data
US 2020/0238074 A1 Jul. 30, 2020

Related U.S. Application Data

(60) Provisional application No. 62/546,468, filed on Aug. 16, 2017, provisional application No. 62/546,494, filed on Aug. 16, 2017.

(51) Int. Cl.
*A61B 5/00* (2006.01)
*A61N 1/36* (2006.01)
(Continued)

(52) U.S. Cl.
CPC ............. *A61N 1/0531* (2013.01); *A61B 5/291* (2021.01); *A61B 5/4094* (2013.01); *A61B 5/686* (2013.01);
(Continued)

(58) Field of Classification Search
CPC .............. A61N 1/0531; A61N 1/36082; A61N 1/36103; A61N 1/36139; A61N 1/36178;
(Continued)

(56) References Cited

U.S. PATENT DOCUMENTS 6,944,501 B1 9/2005 Pless
8,000,795 B2 8/2011 Lozano
(Continued)

OTHER PUBLICATIONS

Berger, Theodore W., et al. "A cortical neural prosthesis for restoring and enhancing memory." Journal of neural engineering 8.4 (2011): 046017. (Year: 2011).*
(Continued)

*Primary Examiner* — Lindsey G Wehrheim
(74) *Attorney, Agent, or Firm* — Snell & Wilmer L.L.P.

(57) ABSTRACT

A hippocampal prosthesis for bypassing a damaged portion of a subject's hippocampus and restoring the subject's ability to form long-term memories. The hippocampal prosthesis includes a first set of hippocampal electrodes configured to receive an input signal from at least one of the subject's hippocampus or surrounding cortical region. The hippocampal prosthesis includes a processing device having a memory and one or more processors operatively coupled to the memory and to the first set of hippocampal electrodes. The processing device being configured to generate an output signal based on the input signal received from the first set of hippocampal electrodes. The hippocampal prosthesis includes a second set of hippocampal electrodes operatively coupled to the one or more processors and configured to
(Continued)

receive and transmit the output signal to the subject's hippocampus.

10 Claims, 24 Drawing Sheets

(51) Int. Cl.
    *A61B 5/291*     (2021.01)
    *A61N 1/05*     (2006.01)

(52) U.S. Cl.
    CPC .......... *A61B 5/6868* (2013.01); *A61B 5/7264* (2013.01); *A61N 1/36082* (2013.01); *A61N 1/36103* (2013.01); *A61N 1/36139* (2013.01); *A61N 1/36178* (2013.01)

(58) Field of Classification Search
    CPC ....... A61B 5/291; A61B 5/4094; A61B 5/686; A61B 5/6868; A61B 5/7264
    See application file for complete search history.

(56) References Cited

U.S. PATENT DOCUMENTS

| | | |
|---|---|---|
| 8,942,809 B2 | 1/2015 | Assaf et al. |
| 2008/0004660 A1* | 1/2008 | Assaf ................. A61N 1/32 607/2 |
| 2013/0346039 A1 | 12/2013 | Song et al. |
| 2017/0042474 A1 | 2/2017 | Widge et al. |
| 2017/0113046 A1 | 4/2017 | Fried et al. |
| 2017/0136240 A1 | 5/2017 | Mogul |

OTHER PUBLICATIONS

International Search Report dated Dec. 14, 2018 in corresponding International Application No. PCT/US2018/000151 filed Aug. 16, 2018; total 4 pages.

Written Opinion of the International Searching Authority dated Dec. 14, 2018 in corresponding International Application No. PCT/US2018/000151 filed Aug. 16, 2018; total 5 pages.

\* cited by examiner

FIRST-ORDER KERNELS

SECOND-ORDER KERNELS

PERFORMANCE OF CLASSIFICATION MODELS

| LABELS | MCC (PATIENT A) | MCC (PATIENT B) |
| --- | --- | --- |
| ANIMAL | 0.71 | - |
| ARTIFACT | 0.29 | - |
| BLUE | 0.03 | 0.44 |
| BUILDING | 0.39 | - |
| GEOMETRIC SHAPES | - | 0.20 |
| GREEN | 0.17 | 0.03 |
| LANDSCAPE | 0.15 | 0.26 |
| NATURAL | - | 0.62 |
| PLANT | 0.62 | 0.24 |
| RED | - | 0.21 |
| YELLOW | - | 0.29 |

FIG. 23

APPARATUS AND METHOD FOR DECODING AND RESTORING COGNITIVE FUNCTIONS

CROSS-REFERENCE TO RELATED APPLICATIONS

The present application is a U.S. National Stage entry under 35 U.S.C. 071 of International Application No. PCT/US2018/000151 filed Aug. 16, 2018, which claims the benefit and priority of U.S. Provisional Application No. 62/546,494, entitled "LARGE-SCALE SPARSE MODEL AND USE FOR MEMORY PROSTHESIS," filed on Aug. 16, 2017, and U.S. Provisional Application No. 62/546,468, entitled "DECODING BRAIN MEMORIES FROM HIPPOCAMPAL SPIKING ACTIVITY," filed on Aug. 16, 2017, which applications are hereby incorporated by reference in their entirety.

GOVERNMENT RIGHTS

This invention was made with government support under Contract No. N66001-14-C-4016 awarded by the Defense Advanced Research Projects Agency (DARPA). The government has certain rights in the invention.

BACKGROUND

1. Field of the Invention

The present disclosure relates to applications in neuroscience and therapy. More particularly, to a hippocampal prosthesis for restoring cognitive functions of a hippocampus and to decoding brain memories resulting from hippocampal spiking activity.

2. Description of the Related Art

The hippocampus is a brain region critical for the formation of long-term episodic memories. Restoring memory functions that have been lost as a result of injuries or disease may benefit from a hippocampal prosthesis. A hippocampal prosthesis that restores hippocampal function depends on an operational model of healthy hippocampal operation, including how brain memories depend on signal transmission in the hippocampus. Prior efforts to create models for decoding memories have been unable to draw correlations between hippocampal activity and memory function suitable for the design and construction of hippocampal prostheses. Thus, the creation of models for the design and construction of hippocampal prostheses has so far remained elusive.

SUMMARY

Disclosed is a hippocampal prosthesis for bypassing a damaged portion of a subject's hippocampus and restoring the subject's ability to form long-term memories. The hippocampal prosthesis includes a first set of hippocampal electrodes configured to receive an input signal from at least one of the subject's hippocampus or surrounding cortical region. The hippocampal prosthesis also includes a processing device that has a memory and one or more processors coupled to the memory and to the first set of hippocampal electrodes. The processing device being configured to generate an output signal based on the input signal received from the first set of hippocampal electrodes. The hippocampal prosthesis also includes a second set of hippocampal electrodes operatively coupled to the one or more processors and configured to receive and transmit the output signal to the subject's hippocampus.

These and other embodiments may optionally include one or more of the following features. The output signal may be based on a multiple-input multiple-output (MIMO) model of spike train transformation. The one or more processors may be configured to optimize the MIMO model with a sparse representation of model coefficients.

The MIMO model may be large-scale. The one or more processors may be configured to estimate the MIMO model using group-lasso estimation. The one or more processors may be configured to implement the group-lasso estimation with a local coordinate descent (LCD) technique.

Also disclosed is a method for bypassing a damaged portion of a subject's hippocampus and restoring the subject's ability to form long-term memories. The method includes receiving, by one or more processors, an input signal from a first set of hippocampal electrodes implanted in at least one of the subject's hippocampus or surrounding cortical region. The method also includes generating, by the one or more processors, an output signal based on the input signal received from the first set of hippocampal electrodes. The method also includes outputting, by the one or more processors, the output signal to a second set of hippocampal electrodes in electrical communication with the subject's hippocampus.

Also disclosed is a method for decoding brain memories from hippocampal spiking activity. The method includes digitizing, by one or more processors, an input signal from one or more hippocampal electrodes implanted in a subject, the input signal having a spatial-temporal spike pattern and is produced during a series of defined memory tasks performed by the subject. The method also includes extracting, by the one or more processors, data from the digitized input signal. The method also includes selecting, by the one or more processors, a memory decoding model based on the defined memory task. The method also includes applying, by the one or more processors, a machine learning function to the extracted data based on the memory decoding model. The method also includes determining, by the one or more processors, a performance measure of the memory decoding model.

BRIEF DESCRIPTION OF THE DRAWINGS

Other systems, methods, features, and advantages of the present invention will be or will become apparent to one of ordinary skill in the art upon examination of the following figures and detailed description. Additional figures are provided in the accompanying Appendix and described therein.

FIG. 23 illustrates the MCC's for various labels used according to an aspect of the invention.

DETAILED DESCRIPTION

Figure 1:
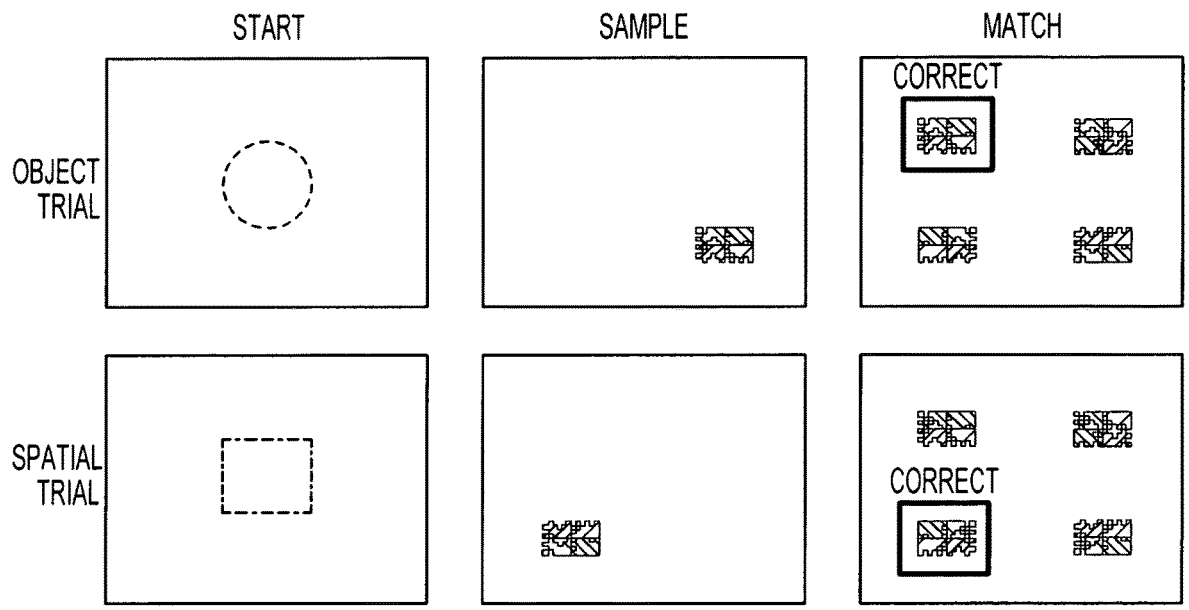
FIG. 1 illustrates delayed match-to-sample (DMS) tasks for human patients containing both Object Trials and Spatial Trials according to an aspect of the invention.
Figure 1:
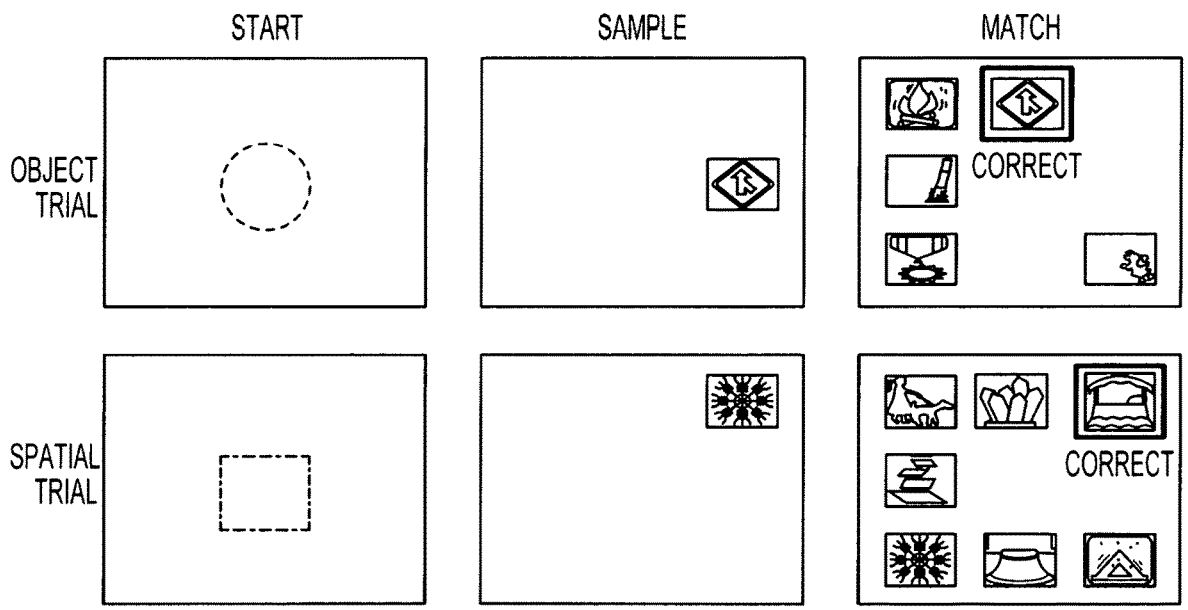

As used herein, "large-scale" means that the brain activity pertains to networks comprised of many neurons, and not to activity at a single neuron or small group of related neurons.
Large-Scale Sparse Model and Use for Memory Prostheses The present disclosure relates to building and using sparse multi-input, multi-output (MIMO) nonlinear dynamical models for modeling large-scale neuronal networks in the brain. The resulting models serve as a computational basis of cortical prostheses for restoring cognitive functions.

The hippocampus is a brain region responsible for the formation of new long-term episodic memories. The hippocampus receives signals carrying short-term memories from neocortices and transforms them with its feedforward pathways into signals that can be stored as long-term memories back in neocortices. If a hippocampal region is damaged due to disease or injury, new long-term memories cannot be formed even though short-term memories remain intact.

A hippocampal memory prosthesis (hippocampal prostheses) may be designed to bi-directionally communicates with the hippocampus and/or surrounding cortical regions by recording input signals from an upstream region (e.g., CA3), and stimulating output signals back to a downstream region (e.g., CA1). If this input-output transformation sufficiently mimics the input-output transformation performed by the intact hippocampus, the damaged hippocampal region may be bypassed with the reinstated hippocampal signals and long-term memory functions would be restored.

Hippocampal prostheses are a specific form of cortical prostheses. Hippocampal prostheses are different from sensory prostheses where the inputs are external sensory (e.g., visual or auditory) signals and the outputs are internal electrical stimulations to the brain or its peripherals. Hippocampal prostheses are also different from motor prostheses where the inputs are internal motor cortical signals (e.g., M1 spike trains) and the outputs are external signals such as movements or muscle activations.

In contrast, cortical prostheses use internal brain signals (i.e., ensemble neural activities or spike trains) which carry highly processed sensory and motor signals, as both inputs and outputs. Computational models that can accurately replicate the transformations from input spike trains to output spike trains then becomes essential for building cortical prostheses. Computational models may be formulated as a multiple-input multiple-output (MIMO) point-process nonlinear dynamical model of spike train transformation.

To develop the above mentioned models, patients (n=3) suffering from pharmacologically refractory epilepsy were first surgically implanted with FDA-approved hippocampal electrodes capable of field potential (macro-) and single-unit (micro-) recordings for localization of seizures. All patients underwent appropriate clinical epilepsy screening evaluations. A frameless BrainLab Cranial Navigation System was used to plan and guide the electrode entry points, stereotaxic electrode trajectories and targets within the CA3 and CA1 sub-regions of each patient's hippocampus. Electrode localization was confirmed using postoperative MRI. Single unit neural activities (i.e., spike trains) were recorded and isolated using the Blackrock Cervello Elite electrophysiological recording system with a raw data acquisition frequency at 30 k samples/sec without filtering, and a spike sorting frequency at 30 k samples/sec with 500-5,000 Hz bandpass filtering.

FIG. 1 illustrates the delayed match-to-sample (DMS) tasks performed by the patients separated into Cambridge Neuropsychological Test Automated Battery (CANTAB) tasks and Clip-Art tasks. Both CANTAB tasks and Clip-Art tasks contain both object trials and spatial trials. In CANTAB tasks, the objects are non-verbalized geometric patterns. In Clip-ART tasks, the objects are verbalized cartoon images. Object and position trials started with circle and square cues that were presented to the patients on a touchscreen. During the sample phase, an object was presented in a specific position of the screen (Sample Presentation) and the patient needed to touch the object in order to form a Sample Response event. In the Match Phase of an object trial, the patient needed to choose and touch the correct object that was seen in the previous Sample Phase among various distractors in order to generate a correct Match Response.

During the Match Phase of a position trial, patients needed to choose and touch the correct position of the object shown in the previous Sample Phase among other positions in order to generate a correct Match Response. Memory functions were evaluated with the percentage of correct responses during a DMS session that consisted of approximately 100 trials. All MIMO models were estimated and validated using CA3 and CA1 data recorded during the DMS tasks. Patients were not recorded when they were not performing the task.

Figure 2:
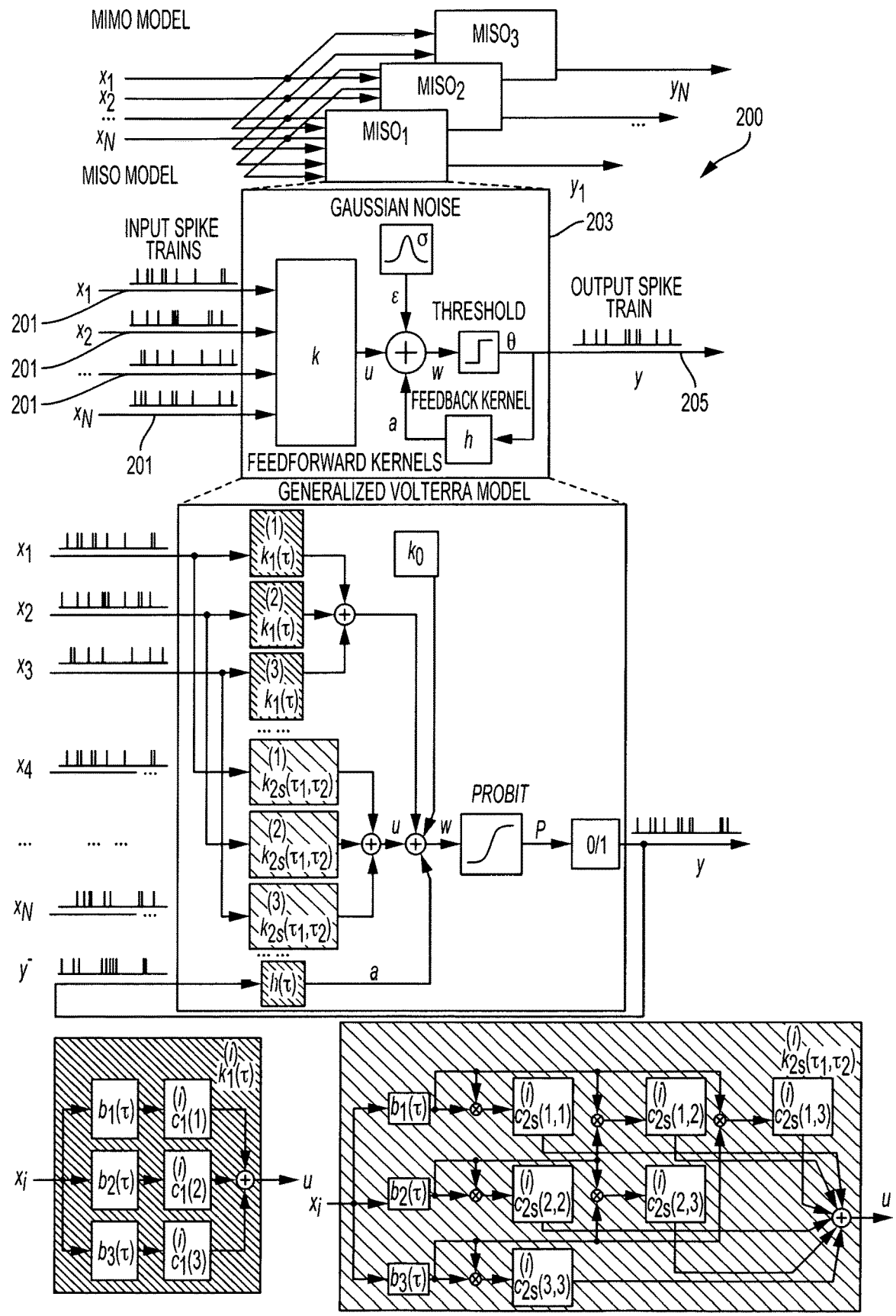
FIG. 2 illustrates a block diagram showing a MIMO nonlinear dynamical model consisting of a series of multiple-input, single-output (MISO) models of spiking neurons that are equivalent to generalized Laguerre-Volterra models according to an aspect of the invention.

FIG. 2 illustrates an estimation of a MIMO model 200 that may be decomposed into a series of multiple-input (201), single-output (205) (MISO) spiking neuron models. The MIMO model uses the identified spatio-temporal pattern transformations from an input region to an output region. The series of MISO models are described by the below equations.

$$w = u(k, x) + a(h, y) + \varepsilon(\sigma) \quad \text{Equation 1}$$

$$y = \begin{cases} 0 & \text{when } w < \theta \\ 1 & \text{when } w \geq \theta \end{cases} \quad \text{Equation 2}$$

$$u(t) = k_0 + \left| \sum_{n=1}^{N} \sum_{\tau=0}^{M} k_1^{(n)}(\tau) x_n(t-\tau) + \sum_{n=1}^{N} \sum_{\tau_1=0}^{M} \sum_{\tau_2=0}^{M} k_2^{(n)}(\tau_1, \tau_2) x_n(t-\tau_1) x_n(t-\tau_2) \right. \quad \text{Equation 3}$$

$$a(t) = \sum_{\tau=1}^{M} h_1(\tau) y(t-\tau) + \sum_{\tau_1=1}^{M} \sum_{\tau_2=1}^{M} h_2(\tau_1, \tau_2) y(t-\tau_1) y(t-\tau_2) \quad \text{Equation 4}$$

In the above equations, variables x and y are input (e.g., CA3) and output (e.g., CA1) spike trains. Feedforward Volterra kernels are described by k which describes the mapping from x to the post-synaptic potential u. Feedback Volterra kernels are described by h which describes the transformation from preceding y to u. Zeroth-order kernel $k_0$ models the input-independent baseline firing rate. First-order feedforward kernels $k_1^{(n)}$ describe the linear relation between the $n^{th}$ input $x_n$ and u, as functions of the time intervals $\tau$ between the past time and the present time.

Second-order feedforward kernels $k_2^{(n)}$ describe the nonlinear interaction between pairs of spikes in the nth input n x as they jointly affect u, in addition to their individual first-order effects. First-order feedback kernel $h_1$ and second-order feedback kernel $h_2$ can be interpreted similarly by treating preceding y as an extra input. N is the number of inputs. M is the system memory length. The total synaptic potential u are added with a feedback after-potential a involving feedback kernels h and preceding output y, and a Gaussian noise $\varepsilon$ with standard deviation $\sigma$, to form the pre-threshold potential w. When w crosses threshold $\theta$, an action potential is generated.

As shown in Equations 3 and 4, Volterra kernels essentially express the systems nonlinear dynamics in a linear form by pre-structuring the nonlinearity in multiplications between their input variables. In addition, the joint effect of the pre-threshold Gaussian noise and the threshold is equivalent to a sigmodal normal cumulative distribution function and a Bernoulli process depicted in FIG. 2, which is equivalent to a probit link function in a generalized linear model. Therefore, this model is termed generalized Volterra model (GVM).

To reduce the model complexity, both feedforward and feedback Volterra kernels were expanded with Laguerre basis functions b depicted in FIG. 2 and represented by the equations below.

$$u(t) = c_0 + \sum_{n=1}^{N} \sum_{j=1}^{J} c_1^{(n)}(j) v_j^{(n)}(t) + \sum_{n=1}^{N} \sum_{j_1=1}^{J} \sum_{j_2=1}^{j_1} c_2^{(n)}(j_1, j_2) v_{j_1}^{(n)}(t) v_{j_2}^{(n)}(t) \quad \text{Equation 5}$$

$$a(t) = \sum_{j=1}^{J} c_1^{h}(j) v_j^{h}(t) + \sum_{j_1=1}^{J} \sum_{j_2=1}^{j_1} c_2^{h}(j_1, j_2) v_{j_1}^{h}(t) v_{j_2}^{h}(t) \quad \text{Equation 6}$$

Figure 3C:
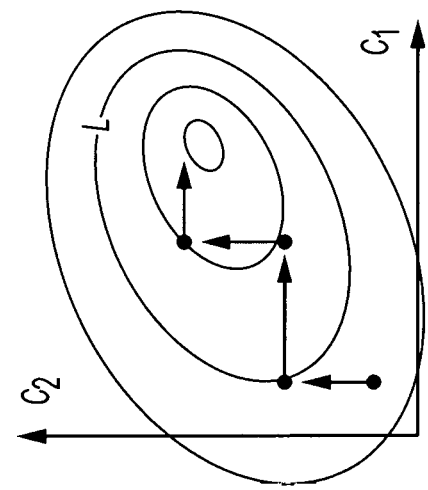
FIGS. 3A-3C illustrate graphs detailing sparse MIMO model estimation achieved by combining Laguerre basis function expansion, group lasso model selection, and local coordinate descent methods according to an aspect of the invention.
Figure 3B:
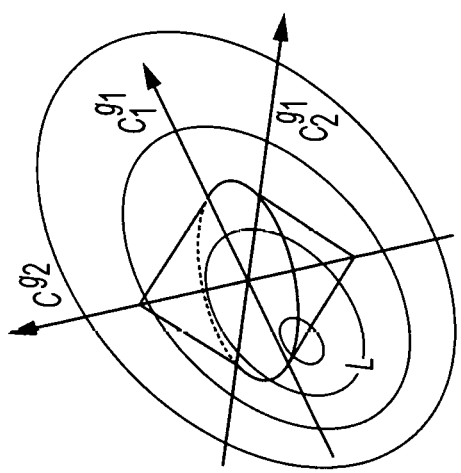
Figure 3A:
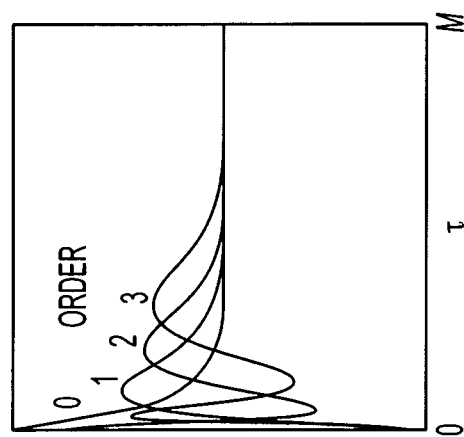

FIGS. 3A-3C illustrate Laguerre basis functions, group lasso formulation, and local coordinate descent respectively. In the above equations, $c_1^{(n)}$, $c_2^{(n)}$, $c_1^{h}$, and $c_2^{h}$ are the sought Laguerre expansion coefficients of $k_1^{(n)}$, $k_2^{(n)}$, $h_1$, and $h_2$, respectively; $c_0$ is simply equal to $k_0$; J is the number of basis functions. Since Laguerre basis functions consists of orthonormal functions with exponentially decaying shapes, as illustrated in FIG. 3A, it can effectively fit a variety of temporal processes with a small number of basis functions. Between three and four Laguerre basis functions are used; M is equal to 500, reflecting a 1 sec memory length with a 2 msec temporal resolution.

To yield sparse representation of the model, model coefficients are calculated with a group regularized estimation method. In this approach, model coefficients are grouped with respect to each input and each model order. Since two model orders, i.e., first-order and second-order are included in this study, there are a total of 2N+2 groups for the N inputs and one output as shown in Equation 7 below. With a group lasso formulation, the coefficients are selected and estimated simultaneously at the group level by minimizing a target function S consisting of the negative log-likelihood $-l$ and a grouped penalty term involving the summation of L2-norm of each group as illustrated in FIG. 3B.

$$S(c) = -l(c) + \lambda \left( \sum_{n=1}^{N} \|c_1^{(n)}(j)\|_2^1 + \sum_{n=1}^{N} \|c_2^{(n)}(j_1, j_2)\|_2^1 + \|c_1^{h}(j)\|_2^1 + \|c_2^{h}(j_1, j_2)\|_2^1 \right) \quad \text{Equation 7}$$

$$l(c) = \sum_{t=1}^{T} [y(t) \log P(t) + (1 - y(t)) \log(1 - P(t))] \quad \text{Equation 8}$$

$$P(c) = \Phi(u(t) + a(t)) \quad \text{Equation 9}$$

In the above equations, $\Phi$ is the normal cumulative distribution function that maps the summation of post-synaptic potential u and after-potential a into the output firing probability P. It is essentially a sigmoidal function that transforms u+a into a value between 0 and 1. T is the data length; $\lambda$ is the sparsity parameter.

Group lasso estimation is implemented with a local coordinate descent (LCD) method, in which the model coefficients are updated one by one along fixed descent directions with line search to minimize the target function as illustrated in FIG. 3C. Since the computational cost increases only linearly with the number of coefficients (i.e., model scale), LCD can be reliably and efficiently applied to solve very large-scale model estimation problems.

In LCD, optimization of model coefficients c is performed by iterating between making a quadratic approximation of the log-likelihood l at the current estimated linear predictor at each step, and individually updating the estimate of each coefficient. The local quadratic approximation of l requires the calculation of second derivative vector w of l with respect to the current estimate of the linear predictor, i.e., $w^{(t)} = \partial^2 l(t)/\partial \Phi^{-1}(\tilde{P}(t))^2$. The calculation of w(t) for the probit link function is given in a previous paper. In LCD, w is recalculated after updating all individual coefficient estimates. The model residual value $\tilde{r}$ is used to accelerate estimation and updated after each coefficient estimate.

For simplicity, in the following we express each group of coefficients $c_1^{(n)}(j)$, $c_2^{(n)}(j_1, j_2)$, $c_2^{h}(j)$, and $c_2^{h}(j_1, j_2)$ as a vector $c_q$ with individual elements $c_{qp}$, where q=1, 2, ... 2N+2 and p=1, 2, ..., $P_q$. $P_q$ is the total number of coefficients in group q. It is apparent that $P_q$ is equal to J and J(J+1)/2 in first-order and second-order groups, respectively. Similarly, all corresponding convolution $v_j^{(n)}(t)$ and $v_j^{h}(t)$, and their element-wise products, $v_{j1}^{(n)}(t) v_{j2}^{(n)}(t)$ and $v_{j1}^{(h)}(t) v_{j2}^{(h)}(t)$, are expressed as $v_{qp}$; the collection of all vectors within a group is expressed as matrix $V_q$, which are all combined to form V. The concatenation of $c_0$ and all $c_{qp}$ is denoted as c. The algorithm for estimating $\tilde{c}$ is described below:
1) Start with a set of the initial values of $\tilde{c}$
2) Calculate w with Equation 10
3) $\tilde{r} = Y - \Phi(V\tilde{c})$
4) $\tilde{c} \leftarrow v_0^T W \tilde{r} / v_0^T W v_0 + \tilde{c}_0$
5) $\tilde{r} \leftarrow \tilde{r} - (\tilde{c}_0 - \tilde{c}_0^*) v_0$
6) For each group $\tilde{c}_q$ a. If $\frac{1}{T}\|\nabla_q^T \tilde{r} + V_q^T V_q c_q\| < \sqrt{P_q} \lambda$ i. $\tilde{r} \leftarrow \tilde{r} + \tilde{c}_{qp} V_q$ ii. Set $\tilde{c}_q = 0$ b. Otherwise, for each $\tilde{c}_{qp}$ i. $\tilde{c}_{qp} \leftarrow \dfrac{\frac{1}{T} v_{qp}^T W \tilde{r} + \frac{1}{T} v_{qp}^T W v_{qp} \tilde{c}_{qp}}{\frac{1}{T} v_{qp}^T W v_{qp} + \lambda_i \sqrt{P_q}/(\|\tilde{c}_q\| + \delta)}$ ii. $\tilde{r} \leftarrow \tilde{r} - (\tilde{c}_{qp} - \tilde{c}_{qp}^*) v_{qp}$ 7) Repeat (2) through (6) until convergence In the above algorithm, * denotes the estimate from the previous iteration; W is a diagonal matrix with elements w; $\delta$ is a small value added to prevent division by zero. In addition, each column of V must be standardized to have zero mean and unit variance before estimation.

The relative importance of the likelihood and the penalty term is controlled by the sparsity parameter $\lambda$ (Equation 7). A larger value of $\lambda$ yields sparser estimation of the coefficients, i.e., more groups of model coefficients are deselected or set to zeros. In this study, $\lambda$ is optimized with a 10-fold cross-validation (CV) procedure. First, the minimal value of $\lambda$ that yields complete sparsity is calculated as:

$$\lambda_{max} = \max_q \frac{1}{T} \frac{\|v_q^T \tilde{r}\|}{\sqrt{P_q}}$$

$\tilde{r}$ is calculated with the $c_0$ only model, i.e., zeroth-order model. A series of 100$\lambda$ values that are logarithmically spaced between $\lambda_{max}$ and $0.01_{max}$ are used to estimate the sparse models and determine the selection path. The $\lambda$ value that yields the smallest out-of-sample negative log-likelihood is selected as the optimal $\lambda$.

Figure 4B:
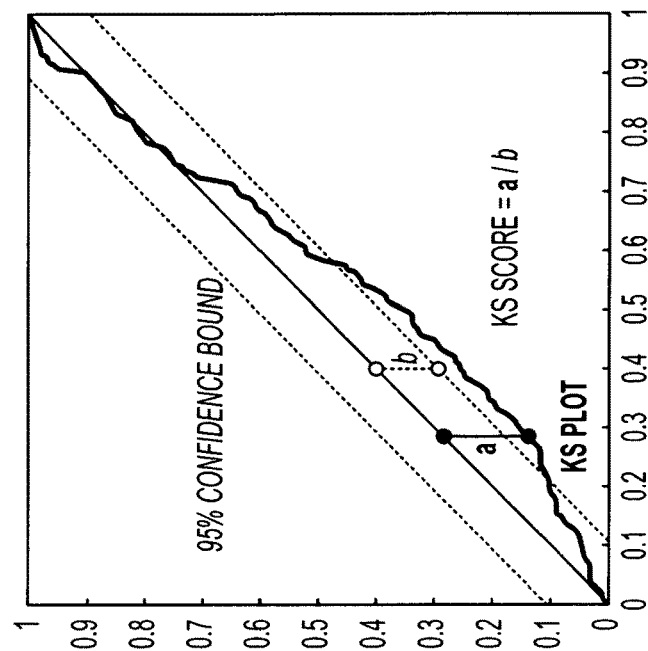
FIGS. 4A-4B illustrate a set of charts detailing a model goodness-of-fit with a Kolmogorov-Smirnov test based on the time-rescaling theorem according to an aspect of the invention.
Figure 4A:
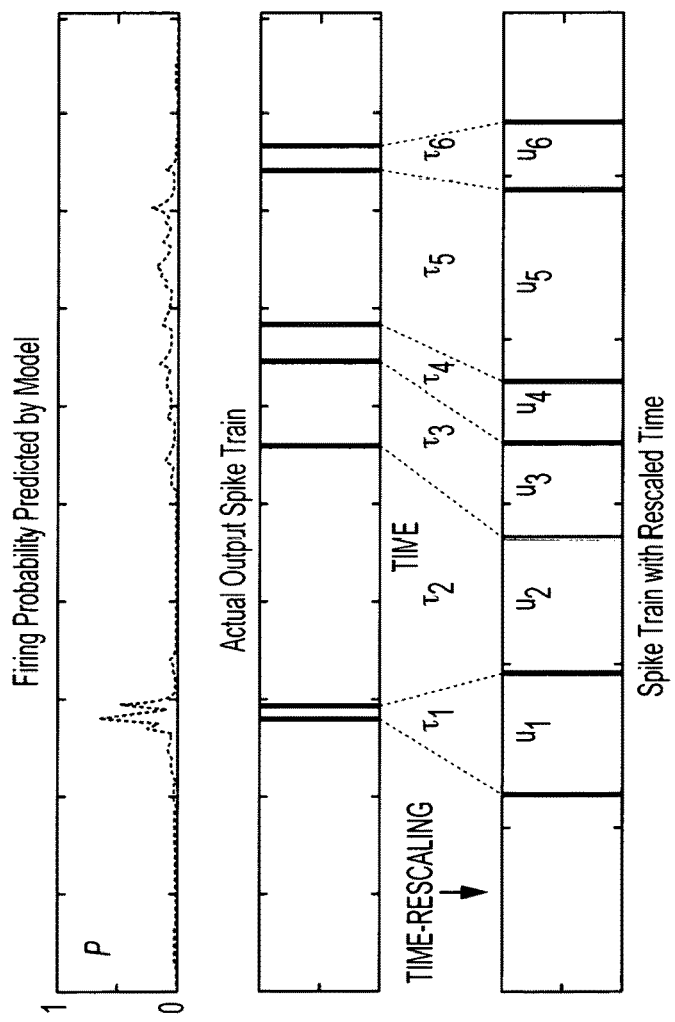

FIGS. 4A-B illustrate the evaluation of a models goodness-of-fit with a Kolmogorov-Smirnov test (KS) based on the time-rescaling theorem. The KS test may be evaluated in terms of the maximal distance between the KS plot and the 45-degree diagonal line. In this study, we use normalized KS-score, i.e., the ratio between the maximal distance between the KS plot and diagonal, illustrated as variable a in FIG. 4B, to the distance between the 95% confidence bound and the diagonal, illustrated as variable b in FIG. 4B, as the final measure. If the normalized KS score is below 1, the KS plot is within the bounds and the model was considered accurate.

To predict y, u is calculated with inputs x and the estimated feedforward kernels. This forms the deterministic part of pre-threshold potential w. A Gaussian random sequence with the estimated standard deviation is then generated and added to u to render w stochastic. At each time t, if w crosses threshold $\theta$, a spike is generated, i.e., y(t) is set to one, and a feedback process a is triggered and added to the future values of w. This is equivalent to transforming u+a into the firing probability $\theta$ and then generate 1 and 0 with a Bernoulli random process as illustrated in FIG. 2. The calculation then moves on to time t+1 with updated w until it reaches the end of the data length.

Figure 5:
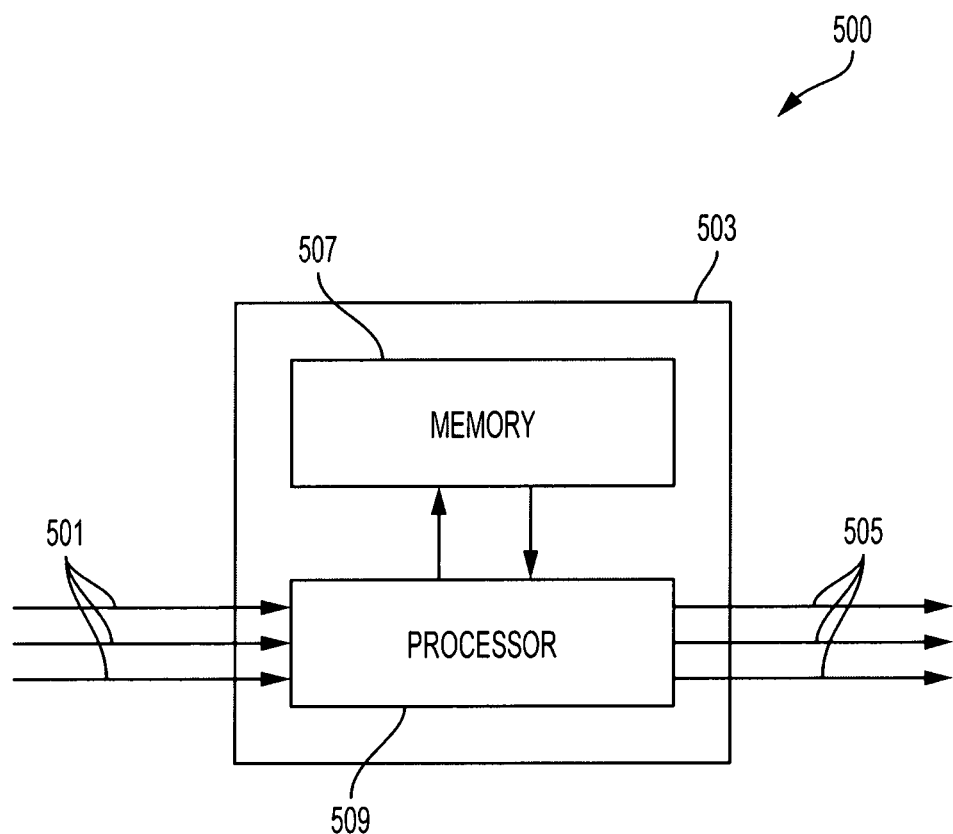
FIG. 5 illustrates an example block diagram of a hippocampal prosthesis for bypassing a damaged portion of a subject's hippocampus and restoring the subject's ability to form long-term memories according to an aspect of the invention.

FIG. 5 illustrates an example block diagram of a hippocampal prosthesis 500 for bypassing a damaged portion of a subject's hippocampus and restoring the subject's ability to form long-term memories using the above mentioned models. The hippocampal prosthesis 500 includes a first set of hippocampal electrodes 501, a processing device 503, and a second set of hippocampal electrodes 505.

The first set of hippocampal electrodes 501 may receive an input signal from a subject's hippocampus and/or the surrounding cortical region. For example, the first set of hippocampal electrodes 501 may be located in the hippocampal CA3 region. The hippocampal electrodes 501 may include a deep large-scale array. The first set of hippocampal electrodes 501 may be implanted within an intact portion of the subject's hippocampus.

The processing device 503 includes a memory 507 and one or more processors 509 operatively coupled to the memory 507 and the first set of electrodes 501. The one or more processors 509 may generate an output signal based on the input signal received from the first set of hippocampal electrodes 501. The output signal may simulate an output signal of a normal hippocampal region originating from the damaged portion of the subject's hippocampus. In some embodiments, the one or more processors 509 may generate the output signal using a multiple-output (MIMO) model of spike train transformation. In some embodiments, the memory 507 may contain an instantiation of a process for estimating a sparse generalized Laguerre-Volterra model for spike train transformations.

The memory 507 may be a non-transitory memory or a data storage device, such as a hard disk drive, a solid-state disk drive, a hybrid disk drive, or other appropriate data storage, and may further store machine-readable instructions, which may be loaded and executed by the one or more processors 509. The memory 507 may store a firmware update to the cortical prosthesis 100.

In some embodiments, an analog-to-digital converter and/or multiplexer may be interposed between the first set of hippocampal electrodes 501 and the one or more processors 509 to condition the input signal from the first set of hippocampal electrodes 501 for digital input to the one or more processors 509. In some embodiments, the analog-to-digital convertor and/or multiplexer may couple to an input port coupled to the one or more processors 509. The input port may be an Ethernet port or a Universal Serial Bus (USB) port.

The one or more processors 509 may transform the input signal using an algorithm stored in the memory 507. The algorithm may include a sequence of more detailed operations, for example, receiving an input signal from the first set of hippocampal electrodes 501, generating the output signal based on the multiple-input, multiple-output (MIMO) model of spike train or equivalent signal feature transformation, and outputting the output signal to the second set of hippocampal electrodes 505.

The one or more processors 509 may optimize the MIMO model with a sparse representation of model coefficients. In some embodiments, the MIMO model may be large-scale and the one or more processors 509 may estimate the MIMO model using group-lasso estimation. In some embodiments, the one or more processors 509 may be configured to implement the group-lasso estimation using a local coordinate descent (LSD) technique.

The second set of hippocampal electrodes 505 may be operatively coupled to the one or more processors 509 and configured to receive and transmit the output signal to the subject's hippocampus. For example, the second set of hippocampal electrodes 505 may be located in the hippocampal CA1 region. The second set of hippocampal electrodes 505 may be implanted within an intact portion of the subject's hippocampus. The second set of hippocampal electrodes 505 are implanted in a different region of the subject's hippocampus and/or the surrounding cortical region than the first set of hippocampal electrodes 501. The different implantations regions of the first set of hippocampal electrodes 501 and the second set of hippocampal electrodes 505 allows a bridging of the intact regions of a subject's hippocampus and bypassing the damaged region of the subject's hippocampus.

In some embodiments, a digital-to-analog converter and/or multiplexer may be interposed between the second set of hippocampal electrodes 505 and the one or more processors 509 to condition the output signal from the one or more processors 509 for analog output to the second set of hippocampal electrodes 505. In some embodiments, the analog-to-digital convertor and/or multiplexer may couple to an output port coupled to the one or more processors 509. The output port may be an Ethernet port or a Universal Serial Bus (USB) port.

The hippocampal prosthesis 500 may include a network access device in operable communication with the one or more processors 509 and a network. The network access device may include a communication port or channel, such as one or more of a Wi-Fi unit, a Bluetooth® unit, a radio frequency identification (RFID) tag or reader, or a cellular network unit for accessing a cellular network (such as 3G or 4G). The network access device may transmit data to and receive data from devices and systems not directly connected to the hippocampal prosthesis 500. The network, may be a Bluetooth Low Energy (BLE) network, a local area network (LAN), a wide area network (WAN), a cellular network, the Internet, or combination thereof.

The features of hippocampal prosthesis 500 may be utilized with any embodiment of cortical prosthesis disclosed herein.

Figure 6A:
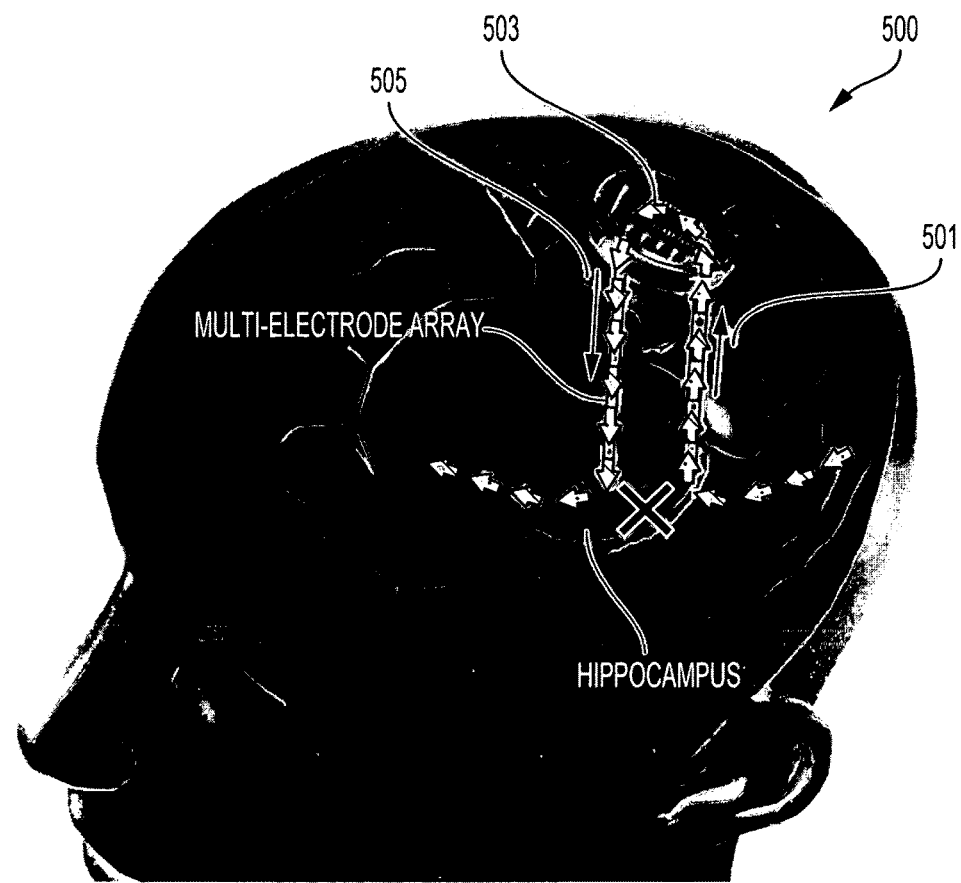
FIG. 6A is an illustration of a hippocampal prosthesis for bypassing a damaged portion of subject's hippocampus and restoring the subject's ability to form long-term memories according to an aspect of the invention.

FIG. 6A is perspective view of the hippocampal prosthesis 500 from FIG. 5 implanted on a patient.

Figure 6B:
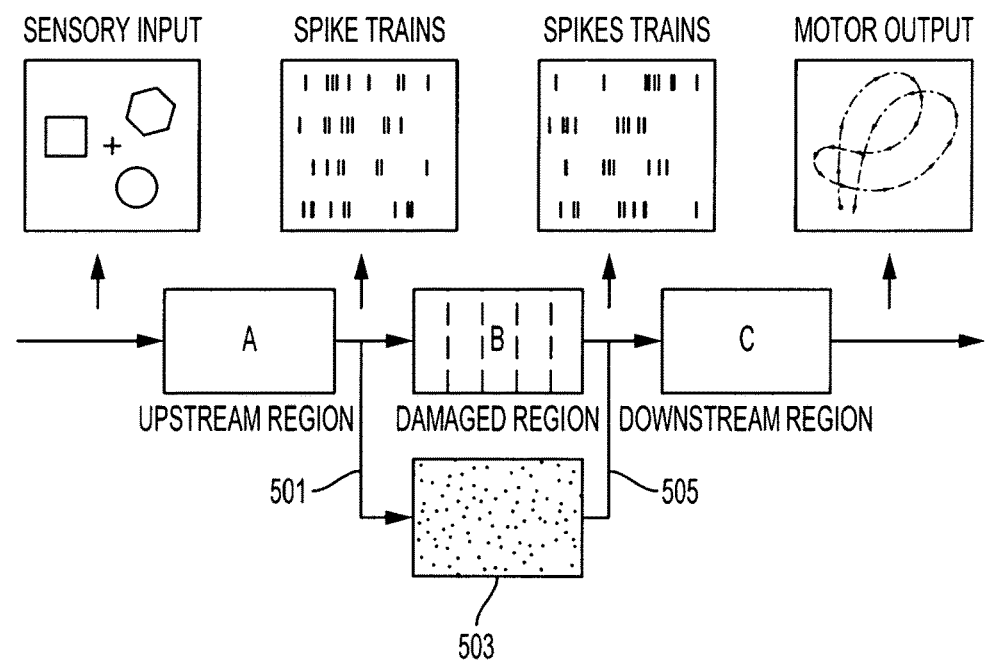
FIG. 6B illustrates an example block diagram of a hippocampal prosthesis bypassing a portion of a subject's hippocampus and restoring the subject's ability to form long-term memories according to an aspect of the invention.

FIG. 6B illustrates the hippocampal prosthesis 500 from FIG. 5 bypassing a damaged portion of a subject's hippocampus. An input signal from an upstream region of a subject's hippocampus is received by the first set of hippocampal electrodes 501. The processing device 503 receives the input signal from the first set of hippocampal electrodes 501 and bypasses the damaged region of the subject's hippocampus. The processing device 503 outputs an output signal to the second set of hippocampal electrodes 505 that are implanted in a downstream region of a subject's hippocampus.

Figure 7:
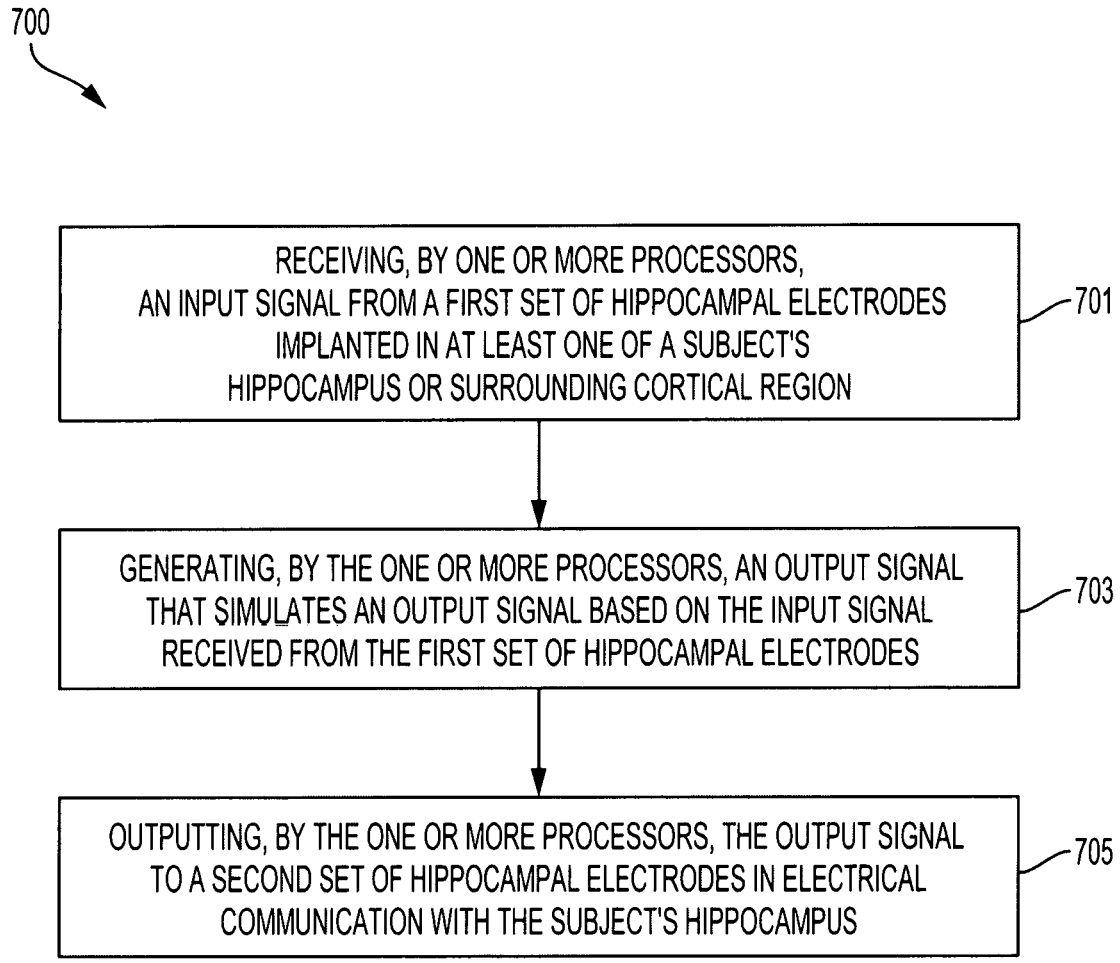
FIG. 7 is a flow diagram of an example process implemented by a hippocampal prosthesis to bypass a damaged portion of a subject's hippocampus and restore the subject's ability to form long-term memories according to an aspect of the invention.

FIG. 7 is a flow diagram of a process 700 implemented by the hippocampal prosthesis 500 to bypass a damaged portion of a subject's hippocampus and restore the subject's ability to form long-term memories.

The one or more processors 509 of the hippocampal prosthesis 500 may receive an input signal from the first set of hippocampal electrodes 501 that are implanted in the subject's hippocampus and/or surround cortical region (701).

The one or more processors 509 of the hippocampal prosthesis 500 may generate an output signal based on the input signal received from the first set of hippocampal electrodes 501 (703). The generated output signal may be based on a multiple-input, multiple-output (MIMO) model of spike train transformation.

In some embodiments, the one or more processors 509 may optimize the MIMO model with a sparse representation of model coefficients. In some embodiments, the MIMO model may be large-scale. The one or more processors 509 may estimate the MIMO model using a group-lasso estimation. In some embodiments, the group-lasso estimation may be based on using a local coordinate descent (LSD).

The one or more processors 509 of the hippocampal prosthesis 501 may output the output signal to the second set of hippocampal electrodes 505 (705). The output signal may simulate an output signal of a normal hippocampal region originating from the damaged portion of the subject's hippocampus.

The features of process 600 may be utilized with any embodiment of process disclosed herein.

Experimental Results

Using the above described methods human hippocampal CA3-CA1 models with spike trains were recorded from epileptic patients performing different forms of the memory-dependent DMS task, i.e., CANTAB and Clip-Art tasks. Depending on the specific surgery procedure, electrode placement, and condition of each patient, various numbers of neurons are recorded. In this paper, we present one set of results from a patient (i.e., Patient A, CANTAB task, unilateral recordings from anterior and posterior hippocampus) with a relatively large number of neurons, and two sets of results from two other patients (i.e., Patient B, CANTAB task, unilateral recordings from anterior hippocampus; Patient C, Clip-Art task, bilateral recordings from anterior hippocampus) with relatively small number of neurons for comparison. Continuous recordings of CA3 and CA1 spike trains are used to estimate and validate the MIMO models. The data lengths of the three patients are 1000, 1000, and 1751 seconds, respectively. To avoid overfitting, only out-of-sample results are shown.

Figure 8:
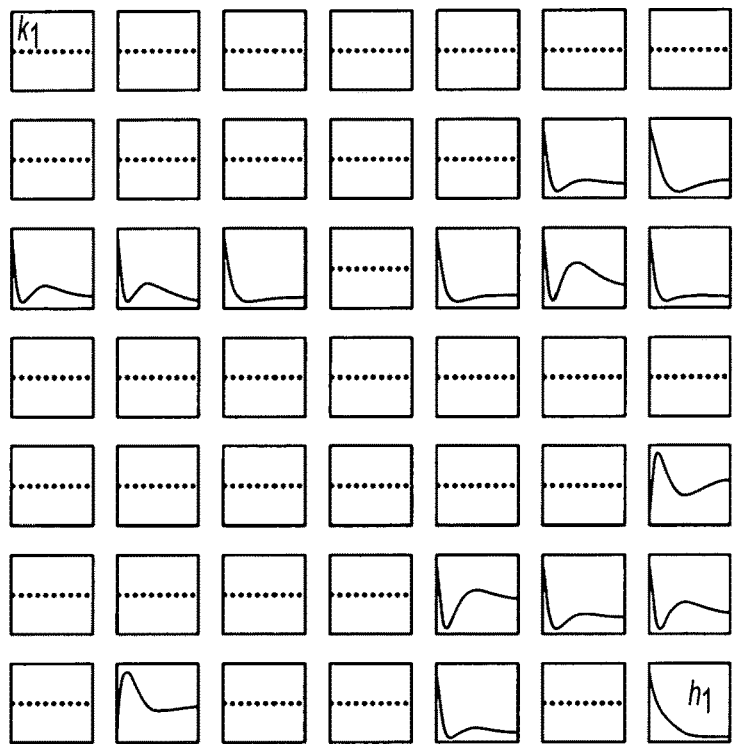
FIG. 8 illustrates a set of charts detailing first-order and second-order feedforward kernels and feedback kernels of a MISO model of the sparse MIMO CA3-CA1 model according to an aspect of the invention.
Figure 8:
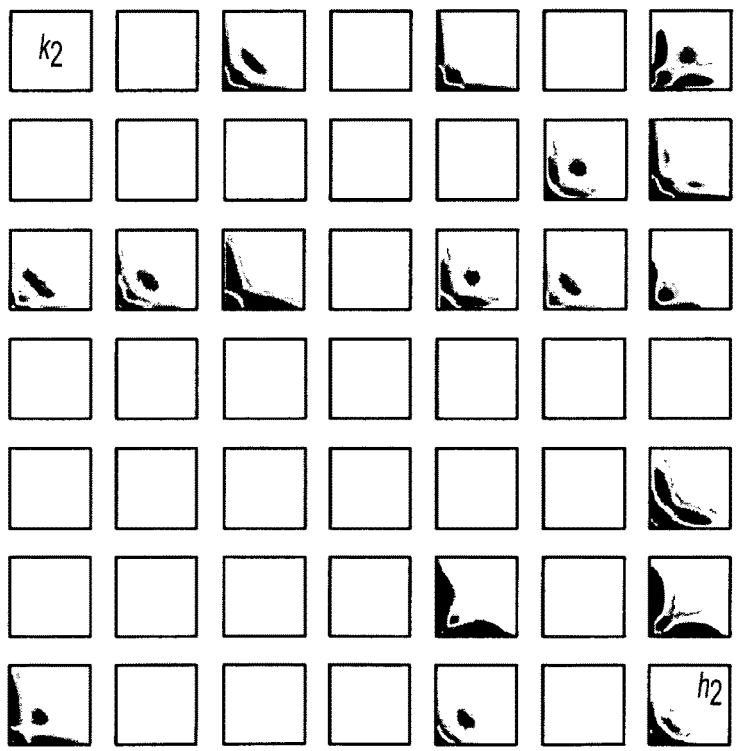

FIG. 8 illustrates the first-order and second-order Volterra kernels (feedforward and feedback) of one representative MISO model. The largest number of neurons were recorded (48 CA3 neurons and 49 CA1 neurons) among the three patients from Patient A. The estimated MIMO model thus contains 49 48-input, single-output models.

First-order kernels k1 are 1-D vectors quantifying the first-order causal relationships between each input (or previous output in the case of feedback kernels h1) and the output as functions of the time intervals, as shown in the top of FIG. 8. Second-order kernels k2 are 2-D matrices describing the second-order joint effects of pairs of input (or previous output in h2) spikes on the output in addition to their individual first-order effects, as shown at the bottom of FIG. 8. In this specific model, among the 48 inputs, 14 inputs show significant first-order kernels, and 16 inputs show significant second-order kernels. It is shown that CA3 neurons are sparsely connected to the CA1 neuron with various kernel shapes and memory lengths. The CA1 neuron has a significant feedback component containing both first-order and second-order kernels.

The goodness-of-fit of this MISO model is evaluated with KS scores. A zeroth-order model, which contains only the mean firing rate of the output, is used as the control. KS scores of zeroth-order, second-order non-sparse, and second-order sparse models are 3.57, 1.71, and 0.99, respectively. This results show that although the non-sparse second-order model can capture a fairly large amount of the system dynamics, it is the sparse second-order model that provides the most accurate prediction among the three models.

MIMO models are formed by concatenating MISO models of each patient. Since cross-validations are used to obtain optimal sparse models, out-of-sample negative log-likelihood values of sparse models are always no larger than those of non-sparse models, and those of non-sparse models are always no larger than those of zeroth-order models. In fact, some non-sparse models even show infinite negative log-likelihood, indicating serious overfitting with the full set of possible coefficients. Sparse models, on the other hand, always reduce out-of-sample negative log-likelihood from their corresponding zeroth-order models. These results are not shown in this paper for simplicity.

Figure 9:
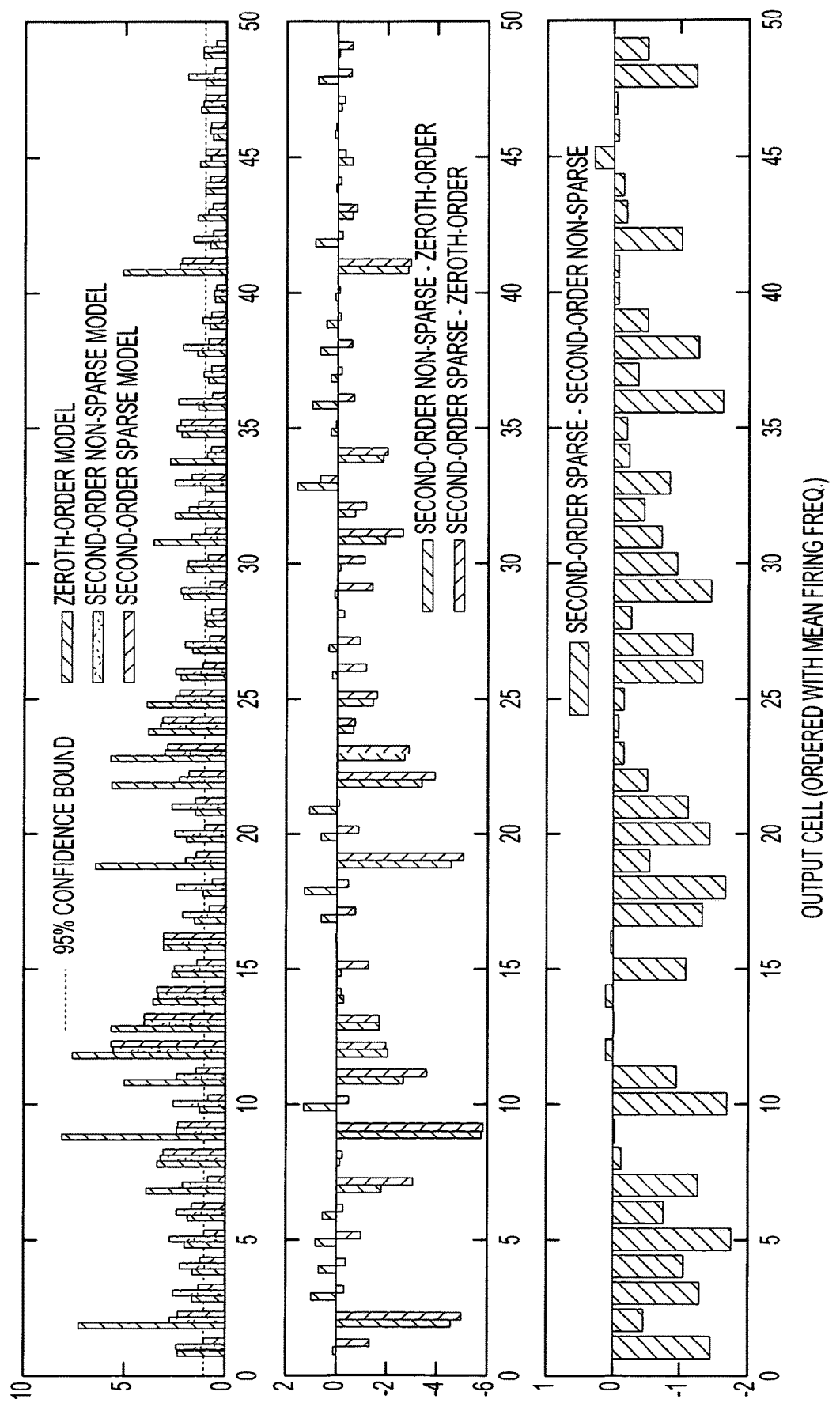
FIG. 9 illustrates graphs detailing normalized KS-scores of MIMO models according to an aspect of the invention.

FIG. 9 illustrates the goodness-of-fits for the models that have been evaluated with an independent measure: out-of-sample normalized KS-scores of each MISO model. In Patient A, out of 49 MISO models, 22 (44.9%) sparse and 7 (14.3%) non-sparse MISO models show a KS plot within the 95% confidence bounds. Sparse models significantly outperform their corresponding non-sparse models in 44 (89.8%) outputs. These results show that sparse models are required for modeling large-scale datasets.

In comparison, Patient B has only 9 inputs and 18 outputs. Out of 18 MISO models, 6 (33.3%) sparse and 5 (27.8%) non-sparse MISO models are within the 95% confidence bounds. Sparse models out-perform their corresponding non-sparse models in 13 (72.2%) outputs. In two outputs, sparse models perform the same as non-sparse models since all inputs are selected in sparse models and make them identical to their corresponding non-sparse models. Patient C has 20 inputs and 23 outputs. Out of 23 MISO models, 10 (43.4%) sparse and 9 (39.1%) non-sparse MISO models are within the 95% confidence bounds. Sparse models out-perform their corresponding non-sparse models in 13 (56.5%) outputs. These results show that in smaller-scale models, the improvements of sparse models over non-sparse models are less significant and the overall performances of MIMO models are not as good as in the larger-scale model, i.e., Patient A, presumably due to the much smaller number of input neurons.

Figure 10:
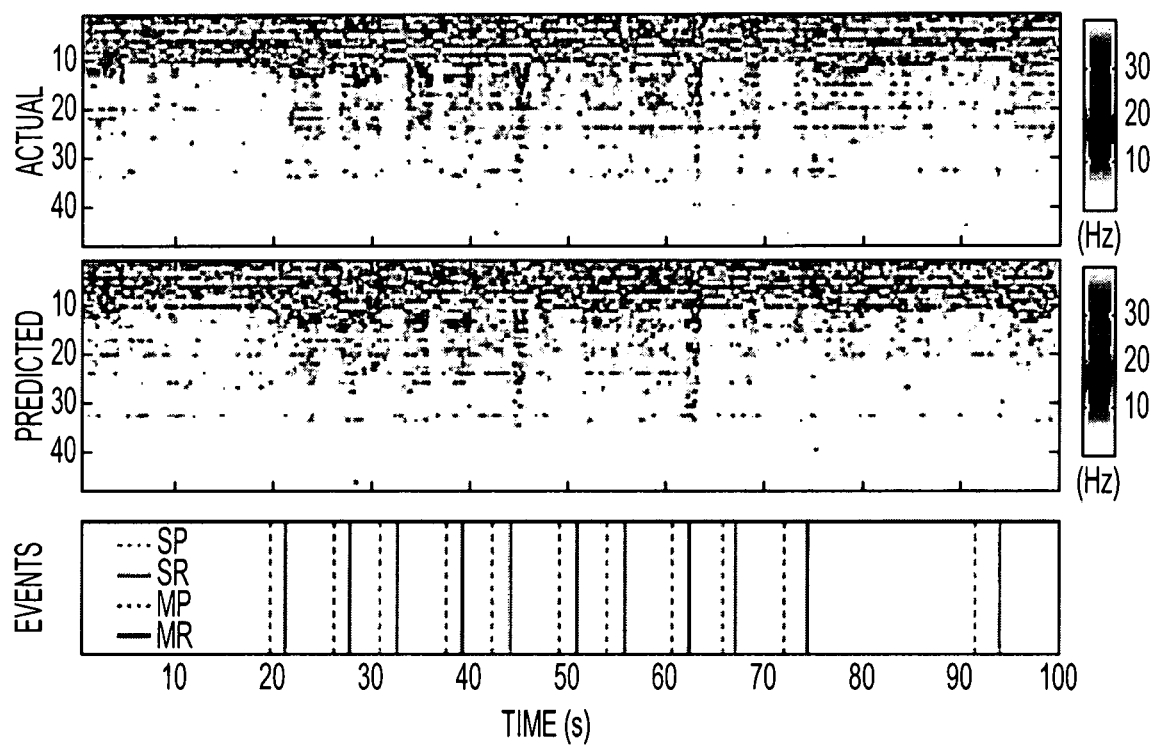
FIG. 10 illustrates a set of charts detailing CANTAB tasks according to an aspect of the invention.
Figure 10:
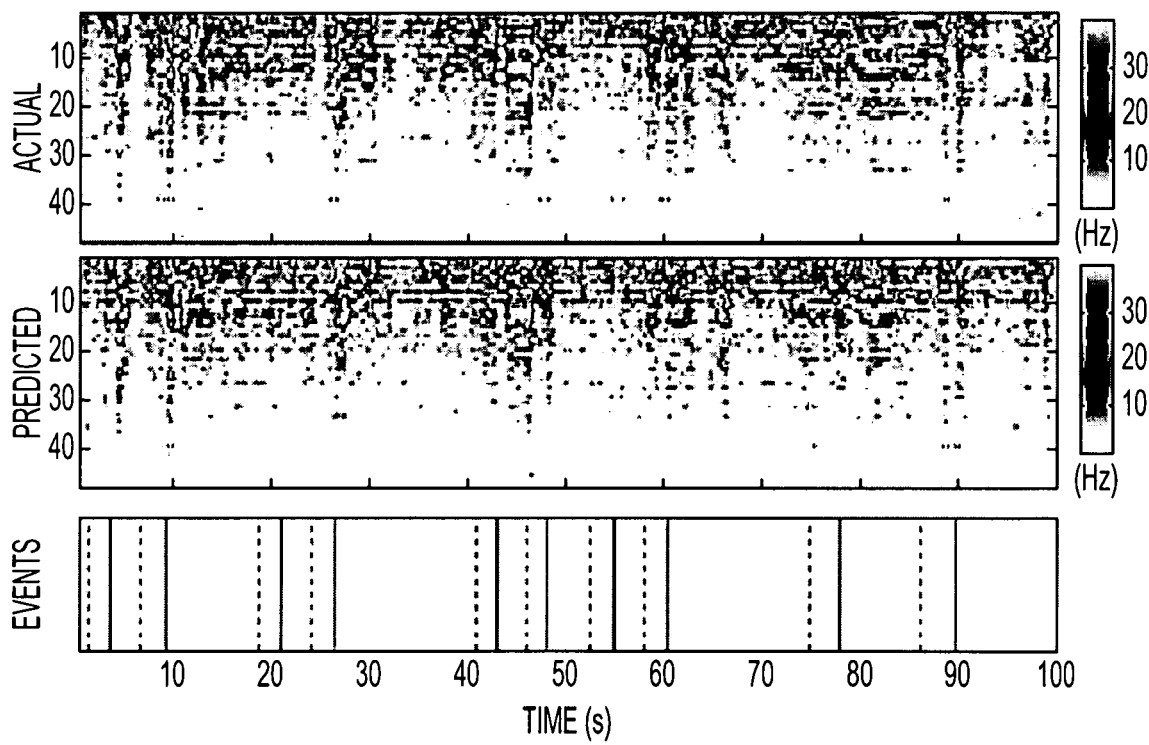

FIG. 10 illustrates CA1 predictions in Patient A. Most importantly, CA1 spatio-temporal patterns are predicted from the CA3 spatio-temporal patterns using the estimated sparse MIMO CA3-CA1 models. Two 100s long segments containing multiple DMS trials are shown. To facilitate visualization, neurons are ordered descending with respectively their mean firing rates. It is evident that this sparse MIMO model can highly accurately predict the CA1 spatio-temporal patterns on a single-trial basis. The prediction captures both the global trend and fine details of the CA1 patterns. The correlation coefficients between the actual and predicted patterns is 0.78.

Figure 11:
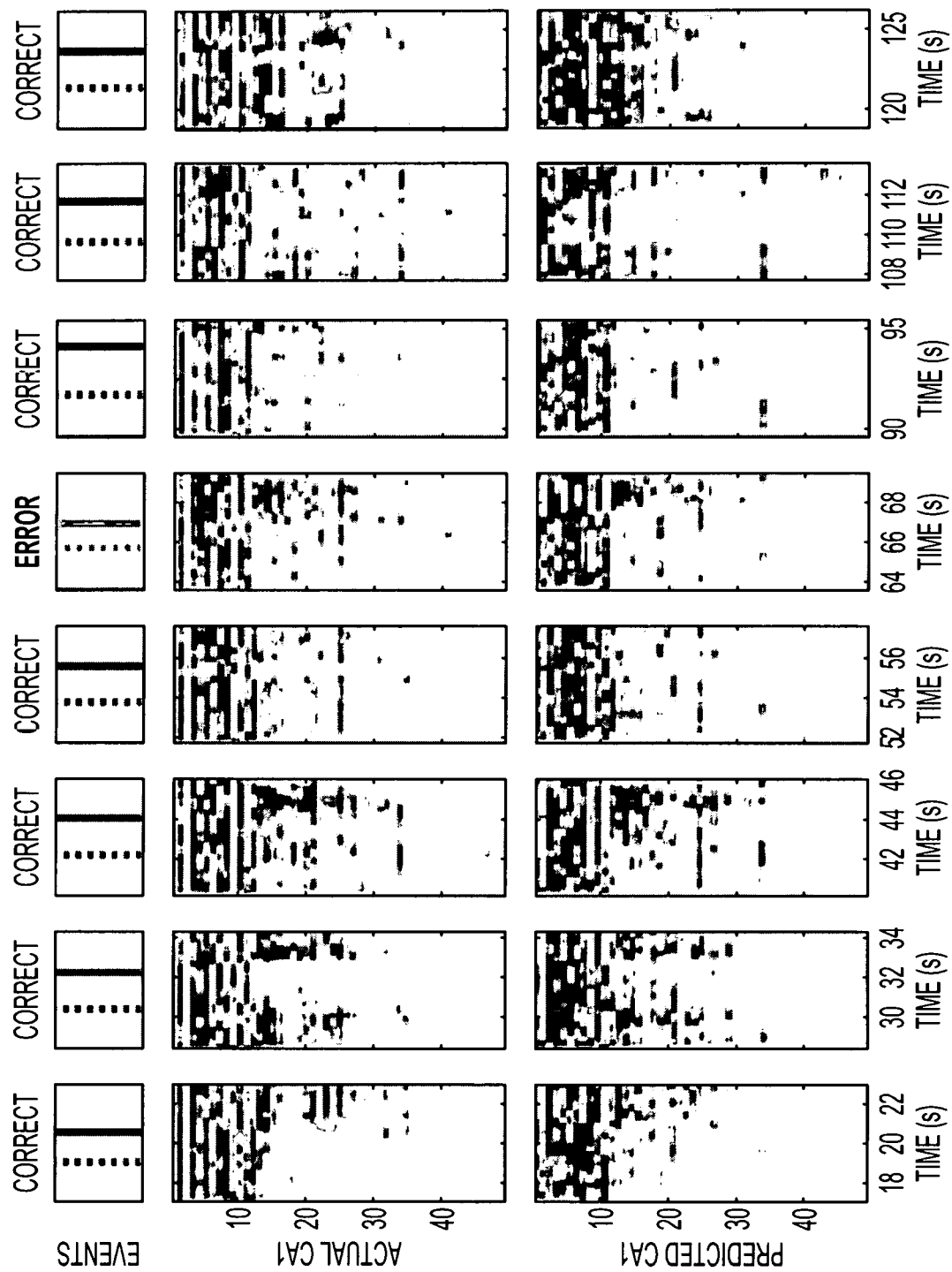
FIG. 11 illustrates a set of charts detailing CANTAB tasks according to an aspect of the invention.

FIG. 11 illustrates spatio-temporal patterns of CA1 activities around Sample Presentation and Sample Response events for Patient A. CA1 neurons consistently exhibit decreased activities before Sample Response events and increased activities afterwards. Despite this general trend, the CA1 patterns also show high degree of variations across different trials. These different patterns presumably encode different objects and object positions that the patient has seen during DMS trials. It is clearly shown that the sparse MIMO model can faithfully replicate these singe-trial CA1 patterns during these critical memory formation periods.

Figure 12:
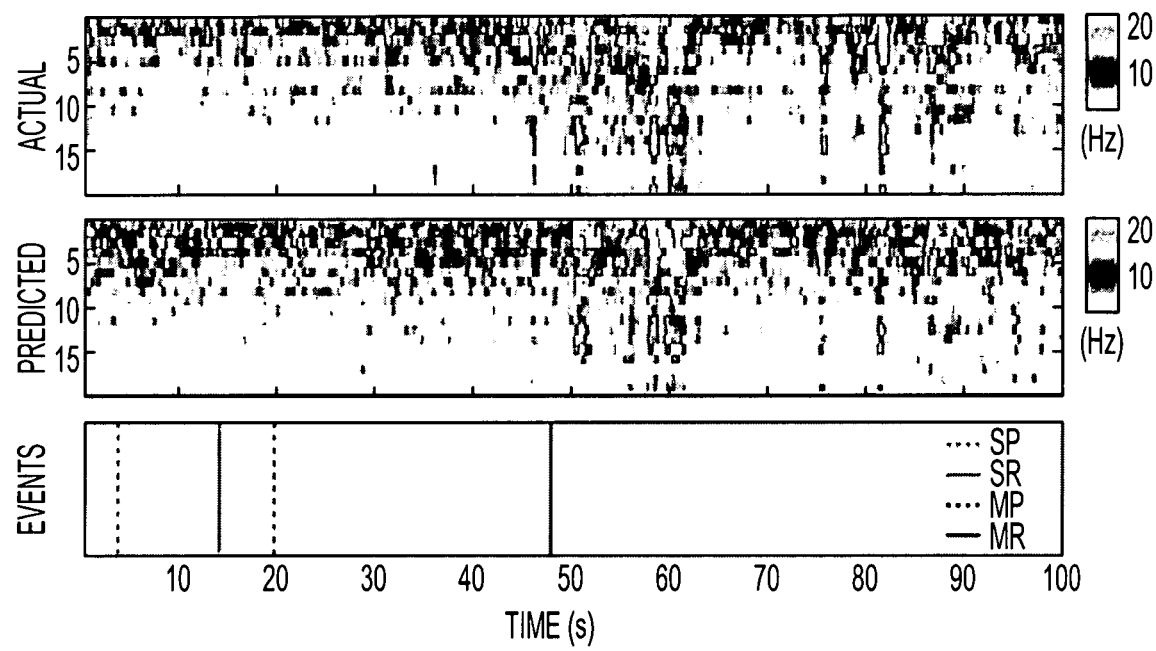
FIG. 12 illustrates a set of charts detailing CANTAB tasks according to an aspect of the invention.
Figure 12:
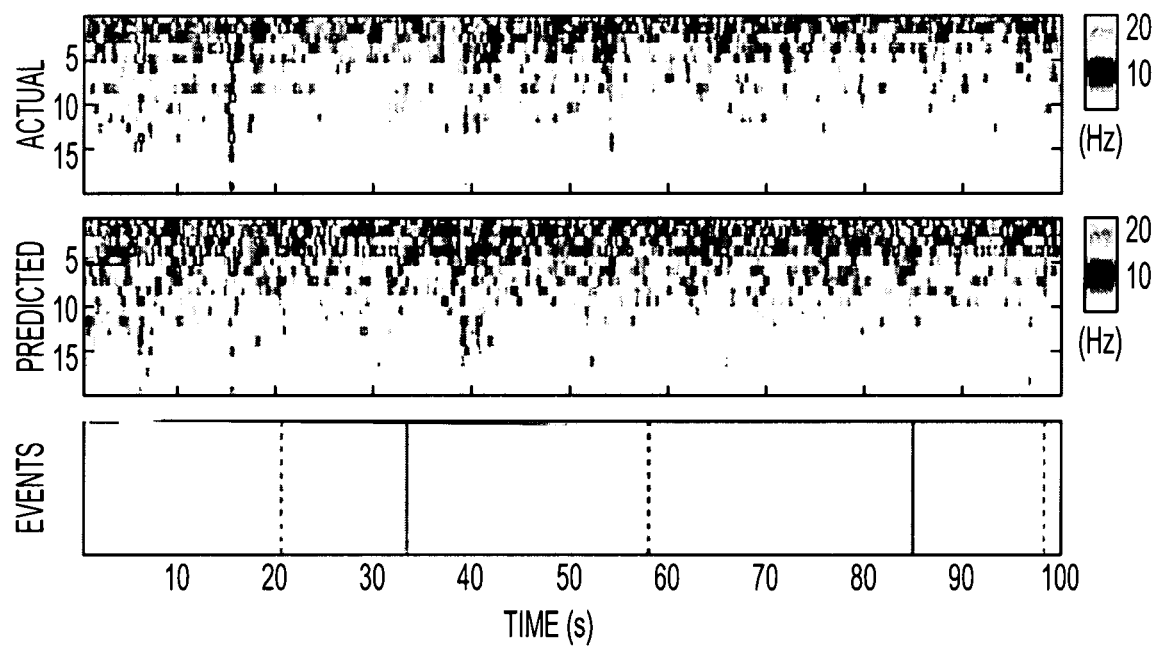

FIG. 12 illustrates CA1 predictions in Patient B. It shown that the sparse MIMO model can still predict the CA1 patterns with a high degree of accuracy, despite the much smaller number of input and output neurons. However, some fine details are missed, especially in the second segment. Clip-Art tasks, instead of CANTAB tasks are used in Patient C.

Figure 13:
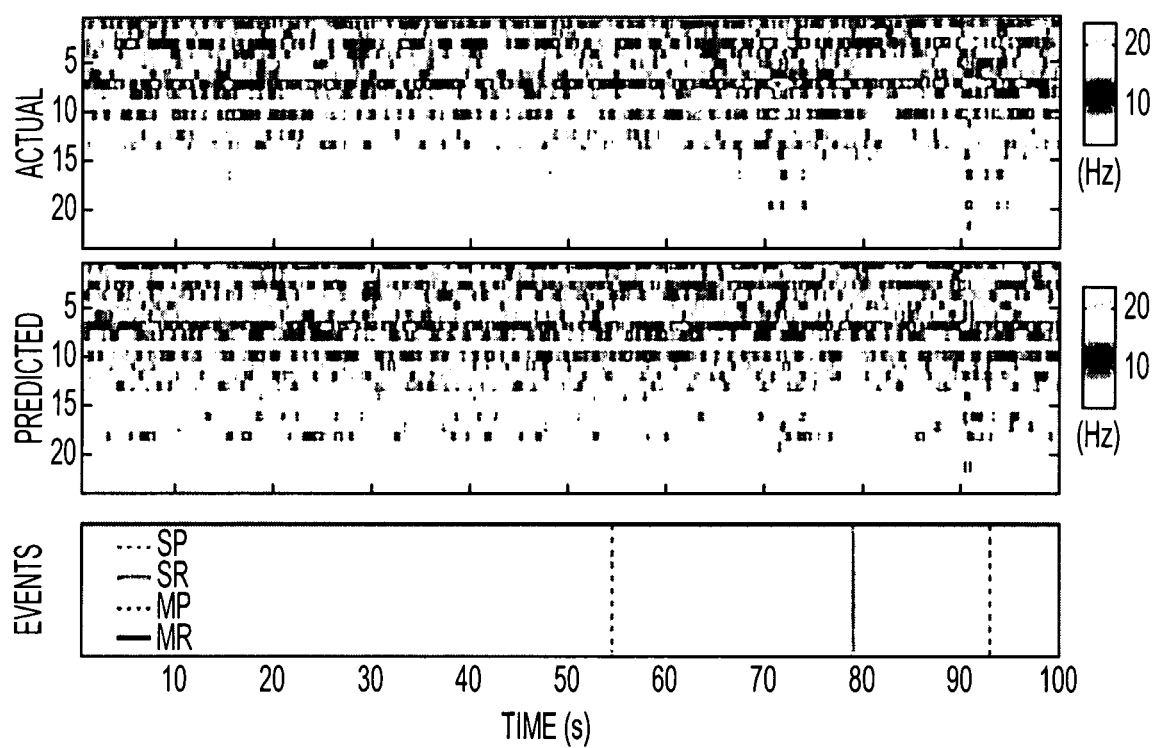
FIG. 13 illustrates a set of charts detailing Clip-Art tasks according to an aspect of the invention.
Figure 13:
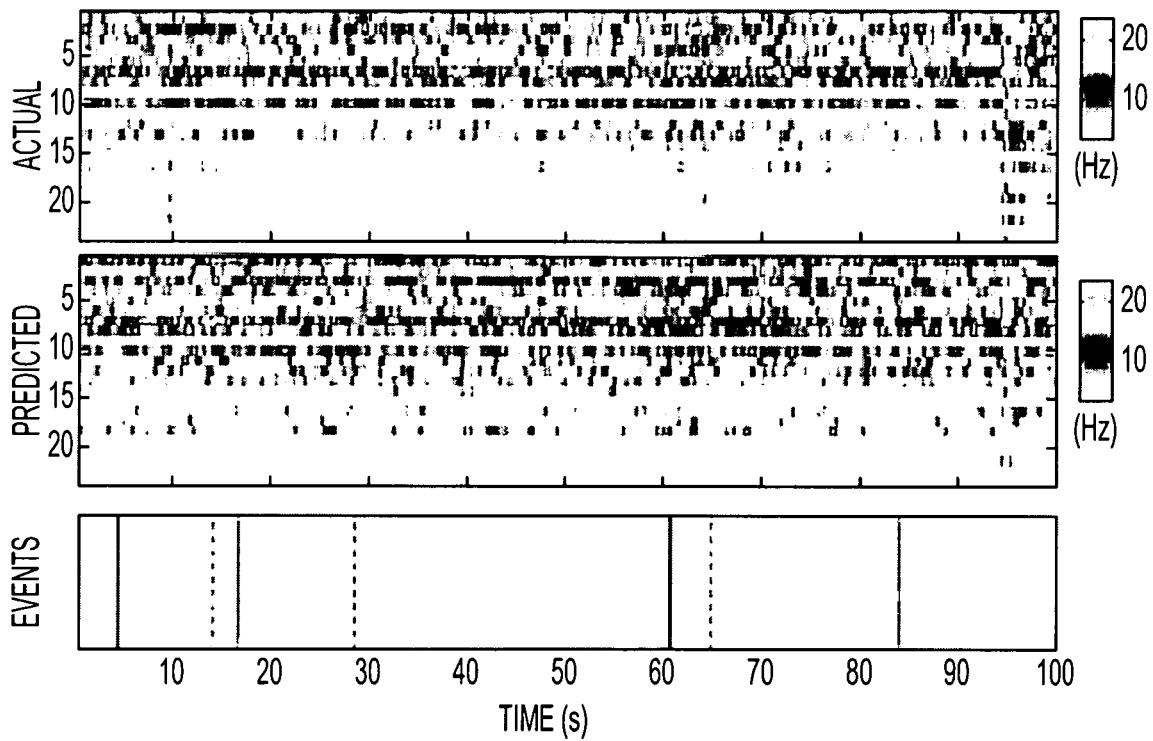

FIG. 13 illustrates variations of firing that are significantly weaker in this dataset compared to those of CANTAB tasks. However, the MIMO model is still able to capture these variations, especially in the high activity ranges.

Decoding Brain Memories from Hippocampal Spiking Activity

The MIMO model of the hippocampus may also be described as a regression model of the relation between input and output spatio-temporal patterns of spikes. In other embodiments, a memory decoding model may be formulated as a classification model relating the spatio-temporal patterns of spikes to the memories represented by the behavior variables.

The above MIMO model relies on three underlying assumptions: 1) episodic memories are encoded in the hippocampal spatio-temporal patterns of spikes, 2) there is sufficient amount of causal relation between the upstream hippocampal signal (e.g., CA3 patterns) and the downstream signals (e.g., CA1 patterns), and 3) electrical stimulation to a subpopulation of hippocampal (e.g., CA1) neurons with the memory patterns can facilitate memory formation. The second and third assumptions have been intensively verified on the heavier of rodents, nonhuman primates, and human subjects.

To build the model for decoding brain memories from hippocampal spiking activity, human subjects were used. Adult patients suffering from pharmacologically refractory epilepsy were surgically implanted with FDA-approved hippocampal electrodes capable of field potential (macro-) and single-unit (micro-) recordings (Ad-Tech Medical Instrumentation Corporation, Racine, Wis.) for localization of seizures. All study participants underwent appropriate clinical epilepsy screening evaluations.

A frameless BrainLab Cranial Navigation System (BrainLab North America, Westchester, Ill.) was used to plan and guide electrode entry points, stereotaxic electrode trajectories and targets within the CA3 and CA1 subregions of each hippocampus. Electrode localization was confirmed using postoperative MRI. Single unit neural activities (i.e., spike trains) were isolated and recorded from the hippocampal CA3 and CA1 regions using Plexon MAP or Blackrock Cervello electrophysiological recording systems.

Figure 14:
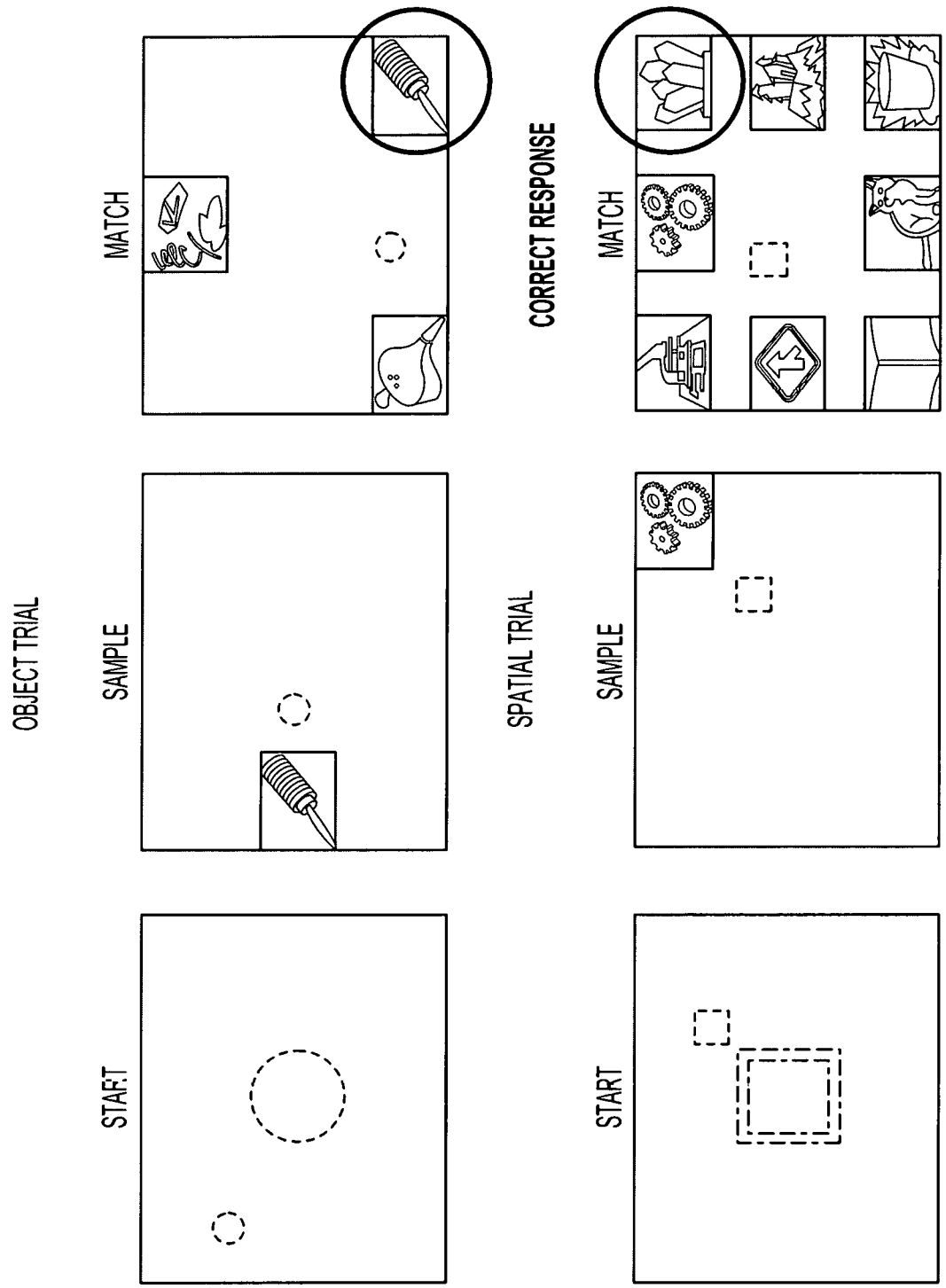
FIG. 14 illustrates delayed match-to-sample tasks according to an aspect of the invention.

FIG. 14 illustrates visual object and spatial position oriented delayed match-to-sample (DMS) tasks used in cognitive and behavioral experiments. Object and position trials start with circle and square cues were respectively presented on a touchscreen (screen). In the Sample Phase, the patient touches an object presented in a specific position of the screen. In the Match Phase of an object trial, the patient needed to choose and touch the correct object that was seen in the Sample Phase among distractors to generate a correct response. In the Match Phase of a position trial, the patients needed to choose and touch the correct position where he/she has seen the object in the Sample Phase among other positions to generate a correct response. Memory functions were evaluated with the percentage of correct responses during a DMS session that consisted of 40-100 trials.

Figure 15:
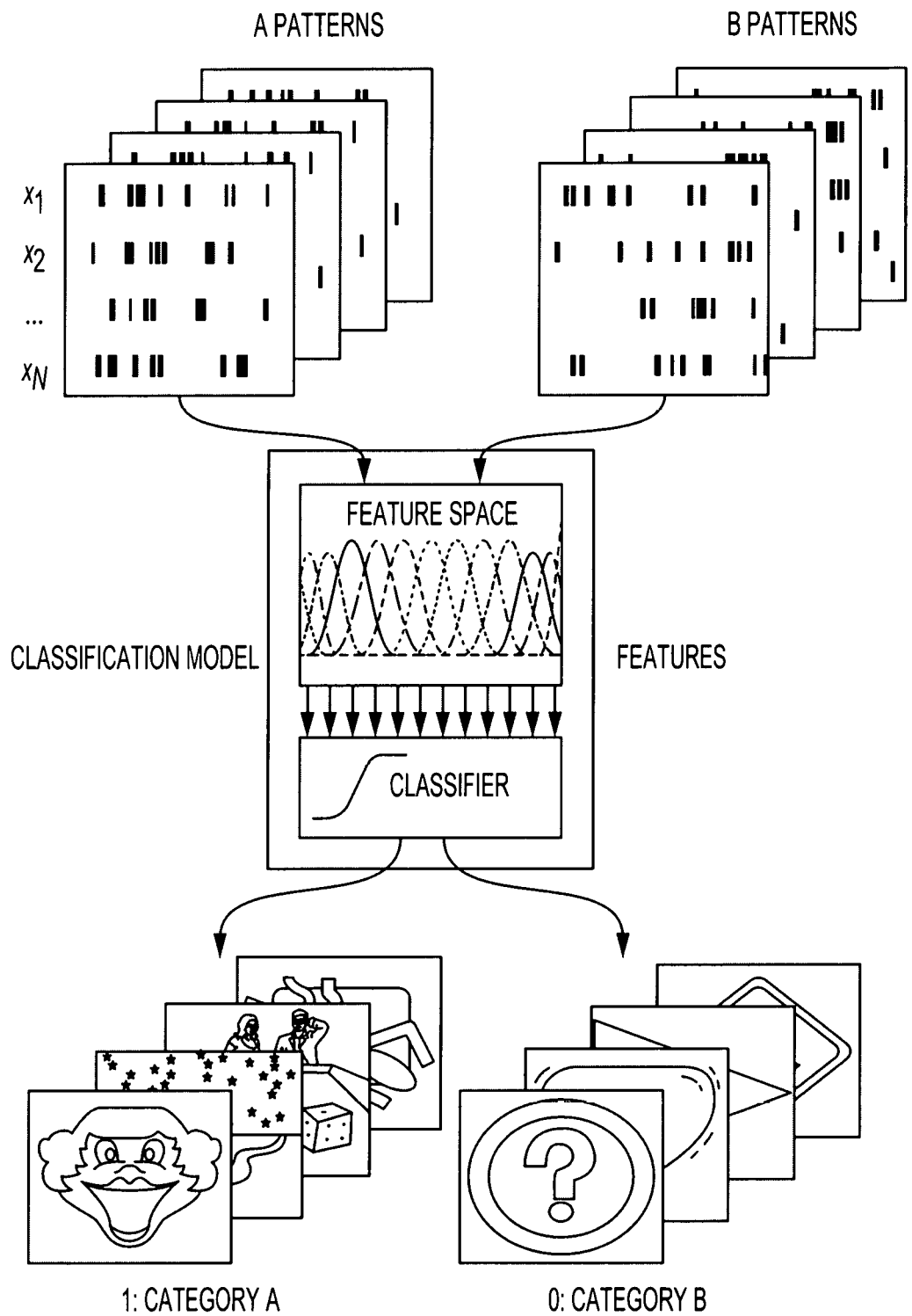
FIG. 15 illustrates a decoding model of hippocampal spatio-temporal patterns of spikes according to an aspect of the invention.

FIG. 15 illustrates the use of B-spline basis functions to extract memory features from the spatio-temporal patterns of spikes recorded from the hippocampal CA3 and CA1 regions. B-splines are piecewise polynomials with smooth transitions between adjacent pieces at a set of interior knot points. The number of knots J controls the temporal resolution of B-splines. Given a B-spline basis B, spike trains x projected to the B-spline feature space via inner product to yield feature vectors z may be described in Equation 11.

$$z^{(n)}(j) = \sum_{\tau=0}^{M} B_j(\tau) x_n(\tau) \qquad \text{Equation 11}$$

In Equation 11, variable M is the time widow for inner product. Variable M was chosen to be from −2 s to +2 s of the sample events. Variable $x_n$ is the nth neuron of the total N neurons included in the analysis. Therefore, z is a 1-by-JN vector. J is optimized in the range of 10 to 200 based on the out-of-sample prediction accuracy.

In other embodiments, spike trains x projected to the B-spline feature space via inner product to yield feature vectors z may be described in Equation 12.

$$z^{(n)}(j) = \sum_{\tau_1}^{\tau_2} B_j(\tau) x_n(\tau) \qquad \text{Equation 12}$$

In Equation 12, the interval [τ1 τ2] is the time widow for inner product, which is chosen to be from −2 s to +2 s of the Sample Response events. Variable $x_n$ is the nth neuron of the N neurons included in analysis. J ranges from of 50 to 150.

Figure 16:
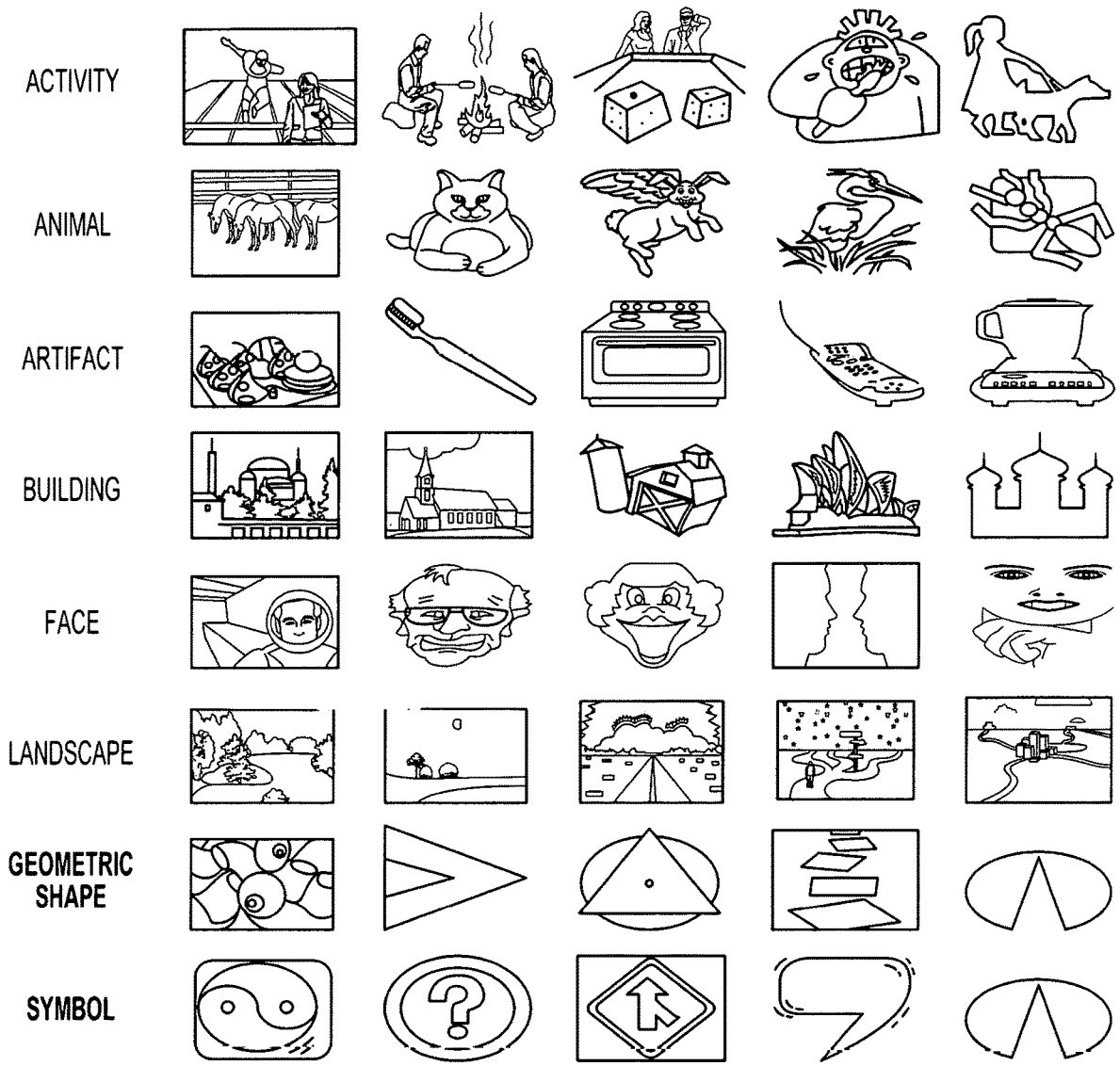
FIG. 16 illustrates images and categories used in the DMS task according to an aspect of the invention.

FIG. 16 illustrates the examples of images and categories used in the DMS task. These images presented in the sample phase were classified by human subjects into 16 non-mutually exclusive categories including: activity, animal, artifact, building, face, geometric shape, human, landscape, language, natural scene, symbol, vehicle, black and white, color, drawing, and natural image. This process produced the target signal for the classification models. The categories including: activity, animal, artifact, building, face, and landscape belong to the naturalistic category. The categories including geometric shape and symbol belong to the abstract category.

Due to the small sample size in this study, these categories were combined into large binary categories such as naturalistic and abstract, where the latter includes geometric shape, language, and symbol categories, and the former contains the rest of categories. The model output is simplified as a binary variable β. The classification model assumed by logistic regression are described in Equations 13 and 14.

$$P(\beta = 1 \mid x) = \left[1 + \exp\left\{-w_0 - \sum_{n=1}^{N}\sum_{j=1}^{J} w^{(n)}(j) z^{(n)}(j)\right\}\right]^{-1} \qquad \text{Equation 13}$$

$$P(\beta = 0 \mid x) = 1 - P(\beta = 1 \mid x) \qquad \text{Equation 14}$$

In Equation 13, variable w is the sought model coefficients where 1 and 0 represent the two classes, respectively. The linear classification rule is described by Equation 15.

$$\beta = \begin{cases} 1 & \text{if}\left\{-w_0 \sum_{n=1}^{N}\sum_{j=1}^{J} w^{(n)}(j) z^{(n)}(j)\right\} < 0 \\ 0 & \text{otherwise} \end{cases} \qquad \text{Equation 15}$$

Compared with the MIMO regression model, the MISO classification model may suffer from serious overfitting problems due to the high dimensional input (typically with hundreds of features) and the relatively small number of data points (80 trials in this study). Therefore, L1 regularization (Lasso) was applied to achieve model sparsity and avoid overfitting as Equation 16.

$$S(c) = -l(c) + \lambda \left(\sum_{n=1}^{N}\sum_{j=1}^{J} \|w^{(n)}(j)\|_2^1\right) \qquad \text{Equation 16}$$

In Equation 16, −l(c) and λ>0 are the negative log likelihood function and the tuning parameter of the classification model, respectively.

In other embodiments, the sparse model estimation may be represented by Equation 17.

$$S(w) = -l(w) + \lambda \left(\sum_{n=1}^{N}\sum_{j=1}^{J} \|w^{(n)}(j)\|_2^1\right) \qquad \text{Equation 17}$$

In Equation 17, −l(w) and λ are the negative log likelihood function and the tuning parameter, respectively. By minimizing S with a 10-fold cross-validation method, λ is optimized and w may be estimated.

For a given B-spline knot sequence in each 10-fold cross-validation trial, one set of w are estimated and used to reconstruct the sparse classification function matrix (SCFM) F with the B-spline basis functions as Equation 18.

$$F^{(n)}(\tau) = \sum_{j=1}^{J} B_j(\tau) w^{(n)}(j) \qquad \text{Equation 18}$$

In Equation 18, F can be directly used to calculate the conditional probability of the modeled label with the input spatio-temporal pattern x as Equation 19.

$$P(\beta = 1 \mid x) = \left[ 1 + \exp\left\{ -w_0 - \sum_{n=1}^{N} \sum_{t=1}^{M} F^{(n)}(\tau) x^{(n)}(t) \right\} \right]^{-1} \qquad \text{Equation 19}$$

Model performance was evaluated with the Matthews correlation coefficients (MCCs). MCC takes into account of the unbalanced data, i.e., the two classes to be classified are of very different sizes. MCC may be calculated from the confusion matrix as Equation 20.

$$MCC = \frac{TP \times TN - FP \times FN}{\sqrt{(TP + FP)(TP + FN)(TN + FP)(TN + FN)}} \qquad \text{Equation 20}$$

In Equation 20, TP, TN, FP, and FN are the numbers of true positives, true negatives, false positives, and false negatives, respectively. The MCC value was between −1 and 1. An MCC of 1 represents perfect prediction; 0 represents no better than random prediction; −1 represents completely opposite prediction.

The averaged SCFM across all temporal resolutions (from $J_{min}=50$ to $J_{max}=150$) and classification trials ($N_{trial}=32$) is calculated as the MCC-weighted summation of individual SCFMs as Equation 21.

$$\bar{F} = N \sum_{i=1}^{N_{trial}} \sum_{J=J_{min}}^{J_{max}} F(i, J) \times MCC(i, J) \bigg/ \sum_{i=1}^{N_{trial}} \sum_{J=J_{min}}^{J_{max}} MCC(i, J) \qquad \text{Equation 21}$$

Equation 21 represents the spatio-temporal characteristics of the classification model estimated with all trials and resolutions. Only F with positive MCC are considered.

Figure 17:
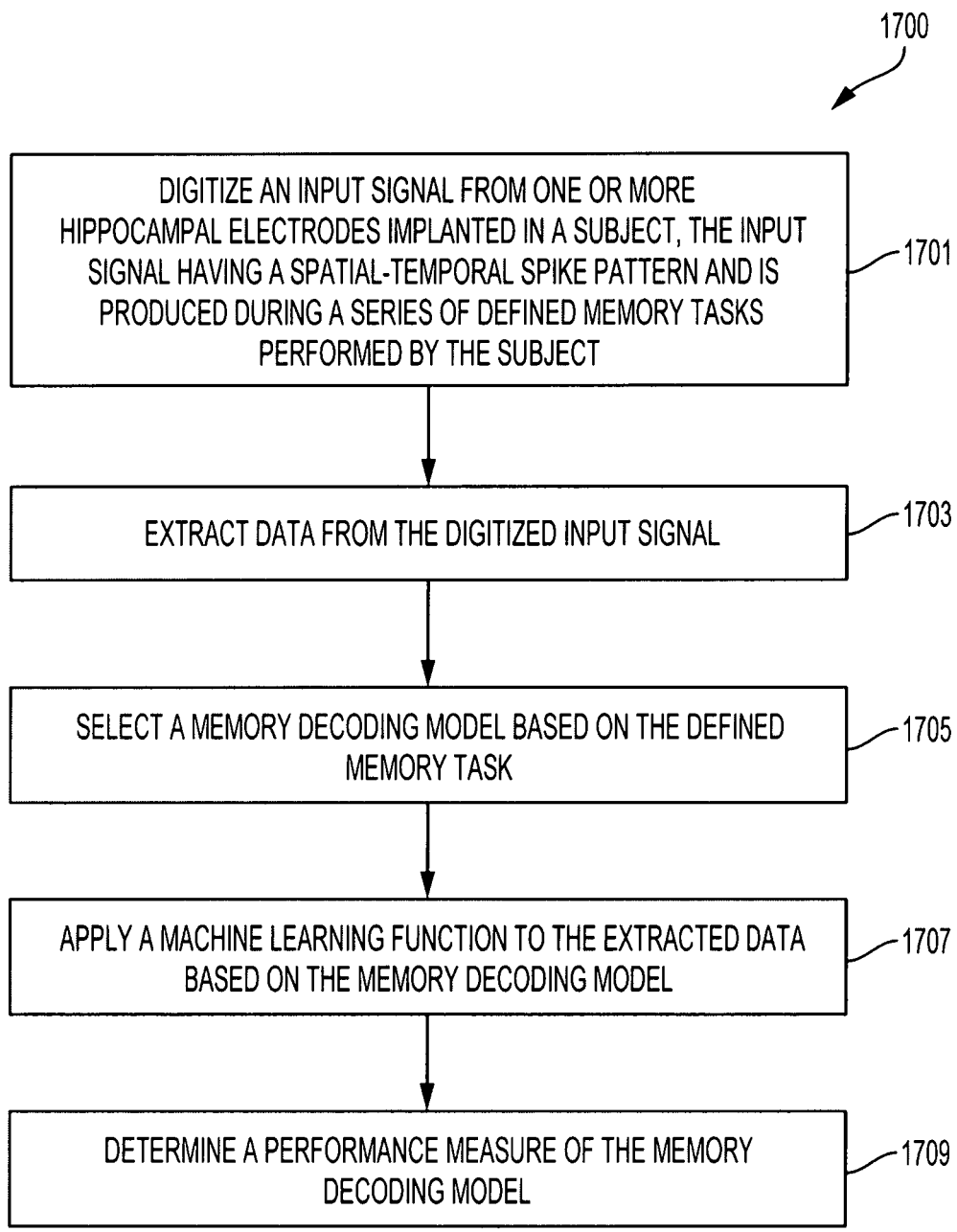
FIG. 17 is a flow diagram of an example process for decoding brain memories from hippocampal spiking activity according to an aspect of the invention.

FIG. 17 is a flow diagram of a process 1700 for decoding brain memories from hippocampal spiking activity.

One or more processors may digitize an input signal from one or more hippocampal electrodes implanted in a subject (1701). In some embodiments the one or more processors may be the processors described in FIGS. 5-7. In other embodiments the one or more processors may belong to a separate apparatus. In some embodiments, the one or more hippocampal electrodes may the first set of hippocampal electrodes 501 described in FIGS. 5-7 that are implanted in the subject's hippocampus and/or surround cortical region. In other embodiments, the one or more hippocampal electrodes may be a different set of electrodes that are implanted in the subject's hippocampus and/or surround cortical region.

In some embodiments, an analog-to-digital converter and/or multiplexer may be interposed between the one or more hippocampal electrodes and the one or more processors to condition the input signal from the one or more hippocampal electrodes for digital input to the one or more processors. In some embodiments, the analog-to-digital convertor and/or multiplexer may couple to an input port coupled to the one or more processors. The input port may be an Ethernet port or a Universal Serial Bus (USB) port.

In some embodiments, a digital-to-analog converter and/or multiplexer may be interposed between the output port and the output device to condition the output signal from the one or more processors for analog output to the output device. In some embodiments, the analog-to-digital convertor and/or multiplexer may couple to an output port coupled to the one or more processors. The output port may be an Ethernet port or a Universal Serial Bus (USB) port.

The one or more processors may be operatively coupled to a memory. The one or more processors may digitize the input signal by executing an algorithm based on program instructions stored in a memory. The memory may be a non-transitory memory or a data storage device, such as a hard disk drive, a solid-state disk drive, a hybrid disk drive, or other appropriate data storage, and may further store machine-readable instructions, which may be loaded and executed by the one or more processors. The memory may store a firmware update to the apparatus.

The algorithm may include a sequence of detailed operations such as detecting one or more analog signals from a network of brain electrodes, converting each of the analog signals to a separate channel (e.g., file, record, or other discrete data object) containing time-correlated digital data and holding the digital data in the memory. In some embodiments, the algorithm may include a sequence of more detailed computational operations. The computational operations may include accessing extracted features of the input signal, applying a sparse logistic regression classifier to classify the features based on the images used in the memory task, and outputting a classification feature matrix or equivalent data structure.

In some embodiments, the processor may be a dedicated hardware or firmware analog-to-digital processor that receives analog data and outputs digital data to a memory cache or storage location.

The one or more processors may generate the input signal while the subject performs different series of defined memory tasks. The one or more processors may administer the series of defined memory tasks to the subject watching a display device by generating a control signal for the display device. In some embodiments, a separate signal generator may generate the input signal while the subject performs different series of defined memory tasks. The input signal may have a spatial-temporal spike pattern that is produced during a serious of defined memory tasks performed by the subject.

In some embodiments, one of the defined memory tasks within the series of defined memory tasks may be selected from at least one of visual object matching, position matching, or object classification. The elapsed time it takes for a subject to complete each defined memory task may be recorded to correlate to the input signal and produce a performance metric for each defined memory task. In other embodiments, a time immediately before, during, and/or immediately after a subject completes a defined memory task may be recorded to correlate to the input signal and produce a performance metric for the defined memory task.

The subject may generate a subject-generated signal that records a time immediately before, during, and/or immediately after a subject completes a defined memory task that is recorded to correlate to the input signal and produce a performance metric for the defined memory task. The one or more processors may record the subject-generated signal as a time-correlated signal, or as a series of events within the input signal. For example, a graphical user interface (e.g., a touchscreen) may be used to present the series of defined memory tasks and the one or more processors may generate data that classifies and timestamps each interaction of the subject with the user interface, and records each interaction in a database or other data structure.

The one or more processors may extract data from the digitized input signal (1703). In some embodiments, the data is extracted from the digitized input signal by fitting a B-spline basis function to the digitized input signal. The one or more processors may vary a number of interior knot points of the B-spline basis function.

Machine learning may be used to correlate the series of defined memory tasks to sparsely classified features of the input signal. Once the correlations are defined for a subject and/or for a class of subject, a hippocampal prosthesis, such as hippocampal prosthesis 500, may be able to process brain stimulation signals that replicate the input signals. In other embodiments, other sparse classification approaches may be used. For example, characterizing signal features such as frequency, phase, and amplitude over short time periods may be used.

In some embodiments, fitting a B-spline model to the input signal may include varying a number of interior knot points of the B-spline basis function. In other embodiments, a different curve fitting approach may be used. For example, a polynomial, trigonometric, or geometric function may be fitted to the input signal.

The one or more processors may select a memory decoding model based on the defined memory task (1705). The defined memory task may be the defined memory task the subject performs during the production of the input signal. The one or more processors may apply a machine learning function to the extracted data based on the memory decoding model (1707). The memory decoding model may be a classification model relating spatio-temporal patterns of brain spiking activity to memories represented by extracted features of the input signal.

In some embodiments, the one or more processors may apply a sparse logistic regression classifier to classify extracted features into memory categories based on the images used in the memory task. For example, the machine learning function may be a sparse logistic regression classifier. The one or more processors may perform regularizing the classifier to avoid overfitting.

The one or more processors may determine a performance measure of the memory decoding model (1709). In some embodiments, the performance measure may which of the different types of memory tasks the subject performed during production of the input signal. In other embodiments, the performance measure may be a correlation coefficient. For example, the correlation coefficient may on Matthews correlation coefficients (MCCs).

The one or more processors may determine a performance measure by executing an algorithm based program stored in the memory. The algorithm may include a sequence of more detailed computations operations. The computational operations may include determining a number of true positives, true negatives, false positives, false negatives, calculating a correlation coefficient (e.g. a Mathews correlation coefficient) based on the determined numbers, and outputting the correlation coefficient to the memory.

The apparatus may include a network access device in operable communication with the one or more processors and a network. The network access device may include a communication port or channel, such as one or more of a Wi-Fi unit, a Bluetooth® unit, a radio frequency identification (RFID) tag or reader, or a cellular network unit for accessing a cellular network (such as 3G or 4G). The network access device may transmit data to and receive data from devices and systems not directly connected to the apparatus. The network, may be a Bluetooth Low Energy (BLE) network, a local area network (LAN), a wide area network (WAN), a cellular network, the Internet, or combination thereof.

The features of process 1700 may be utilized with any embodiment of process disclosed herein.

Experimental Results

Memory decoding models were built for patient No. 9 with respect to two different memory features. The DMS task contains 80 trials in total. Each trial involved one sample image and multiple distractors. In order to perform the DMS task successfully, the patient needed to remember (i.e., form a memory codes of) the sample images or their locations during the Sample phase, depending on the trial type, to generate correct responses in the Match phase. Therefore, the model inputs were CA3 and CA1 spatio-temporal patterns of spike during sample phase, while the model outputs are the binary labels of the sample images for the category to be analyzed. For patient No. 9, 25 CA3 neurons and 12 CA1 neurons were recorded.

The memory decoding model for decoding the memory context, i.e., trial type was built first. The 80 trials were divided into two classes that contained 61 object trials and 19 spatial trials, respectively. The goal of the sparse classification model was to predict the trial type, i.e., object or spatial, based on the CA3 and CA1 spatio-temporal patterns.

Figure 18:
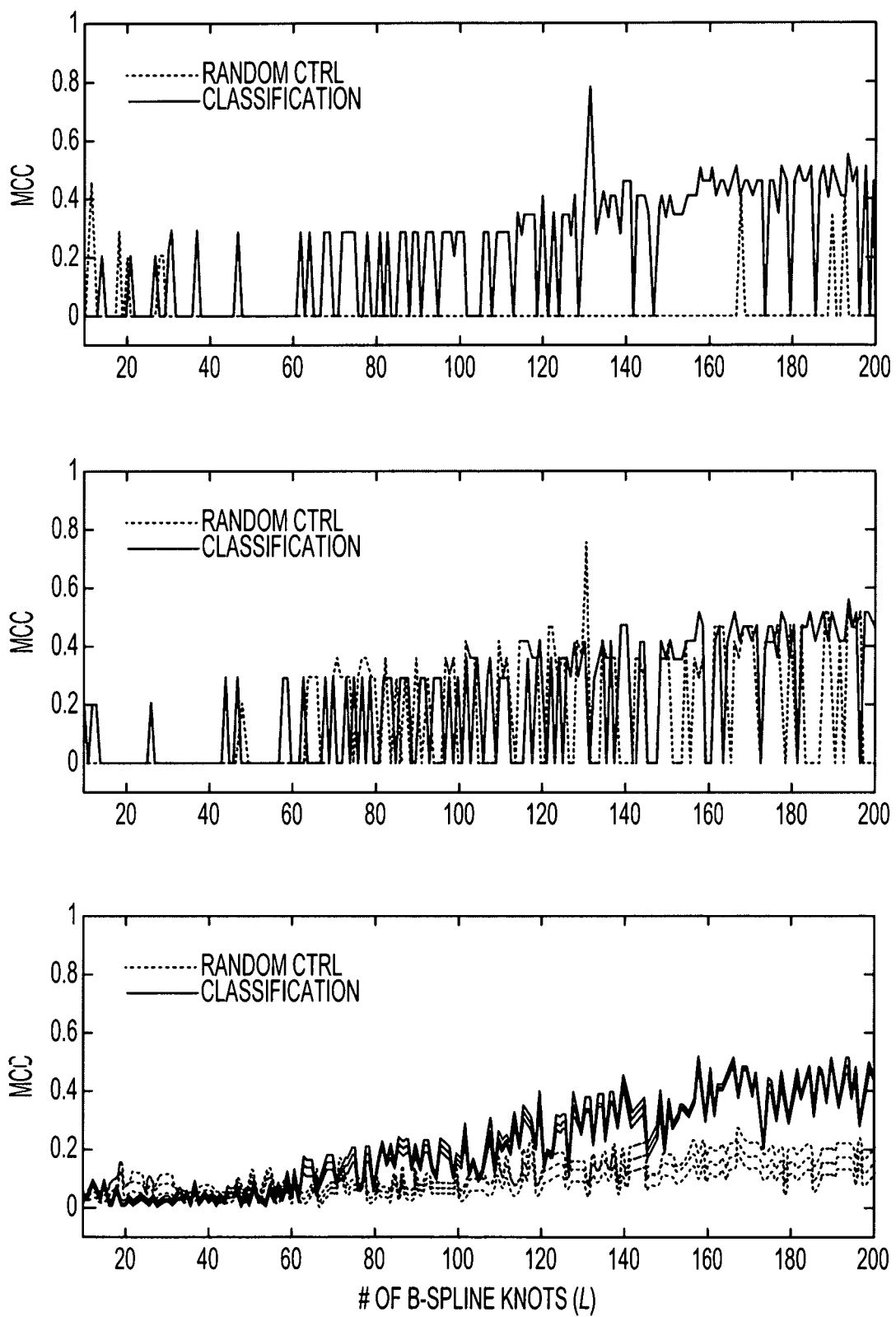
FIG. 18 illustrates performance classification models in decoding memory contexts according to an aspect of the invention.

FIG. 18 illustrates the performance classification models in decoding the memory contexts. Dashed lines represent the MCC's of negative control (Random CTRL) and the solid lines represent the MCC's of the classification models (Classification).

Sparse classification models were estimated for each number of knots L in the range of 10 to 200. Model sparsity of each model was optimized with a 10-fold cross validation procedure. MCCs were plotted against L to evaluate the model performance (Classification). As a negative control, classification was also performed on the same set of spatiotemporal patterns with the category randomly labelled (Random CTRL). Results showed a high level of variability in classification MCCs for different L values with an overall trend of increasing as L increases. In addition, MCC performance also varied across different classification trials, due to the randomness in the cross-validation procedure. By contrast, random control did not show significant classification power, i.e., their MCCs fluctuate around 0 with no obvious trend of increasing with L, as shown in the top two plots of FIG. 18.

The mean MCC results from the 32 classification trials, bottom plot of FIG. 18, shows that the sparse classification model may extract significantly amount of information about the memory task trial type from the hippocampal CA3 and CA1 spiking activities.

Additional memory decoding models were built for the memory content. The 80 trials were divided into two classes containing 63 Naturalistic trials and 17 Abstract trials. The goal of the sparse classification model was to predict whether the sample image of each trial is naturalistic image or abstract image, based on the CA3 and CA1 activities.

Figure 19:
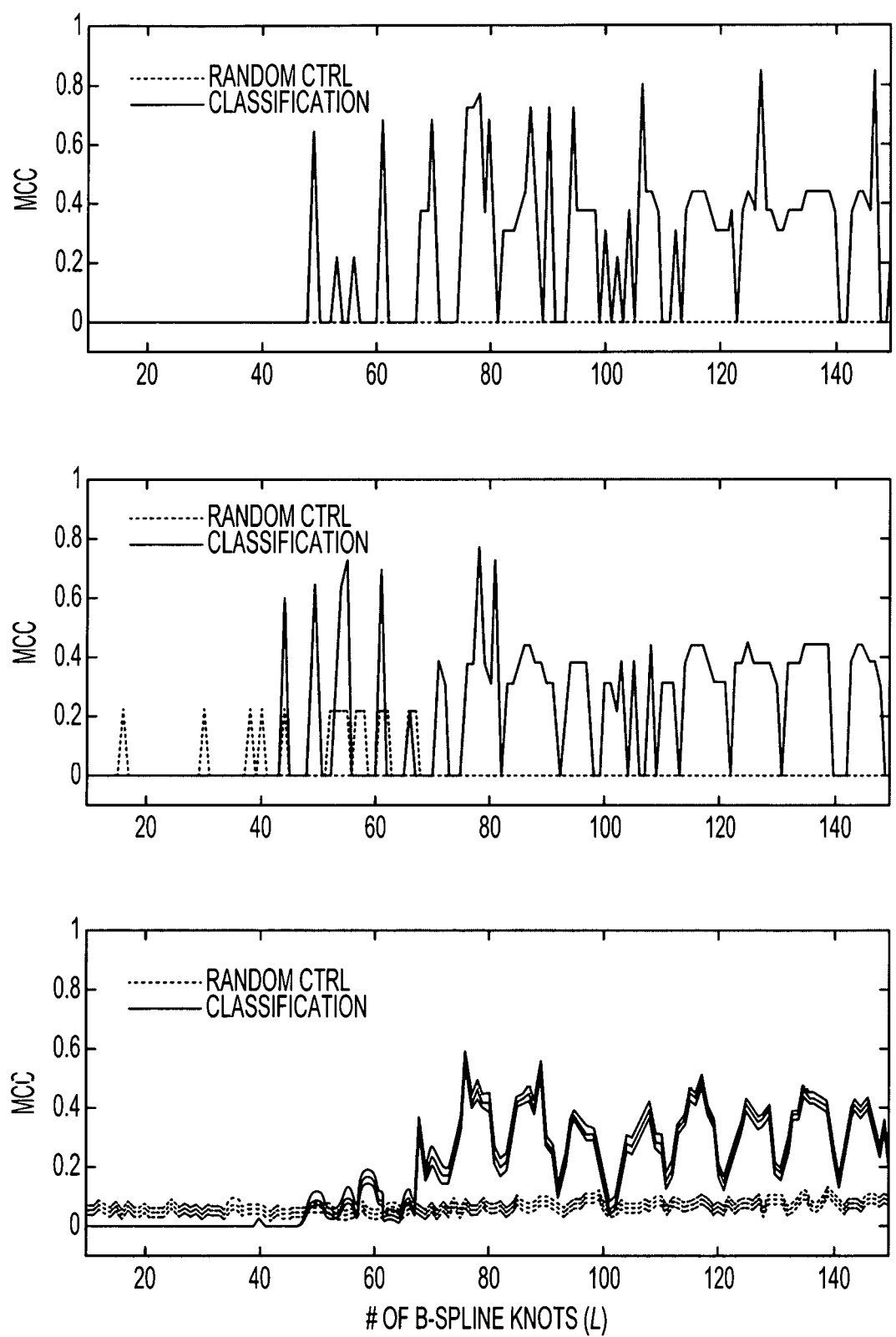
FIG. 19 illustrates performance classification models in decoding memory content according to an aspect of the invention.

Similar to the previous results, it was shown that the sparse classification model can distinguish the two types of sample images significantly above the chance level when the L value is sufficiently high, despite the variability of MCCs in single trials, as illustrated in FIG. 19.

FIG. 19 illustrates the performance classification models in decoding memory content. Solid lines represent the MCC's of classification models and the dashed lines represent the MCC's of negative control.

The above results show that, despite the high level of variations, sparse classification models can extract a significant amount of information about memory features with sufficiently high feature temporal resolutions and the regularized estimation method. In the Naturalistic vs. Abstract classification, the MCCs show a marked periodicity. This periodicity may have been caused by some form of aliasing in the interaction between splines interpolants and the neural signals.

Figure 20:
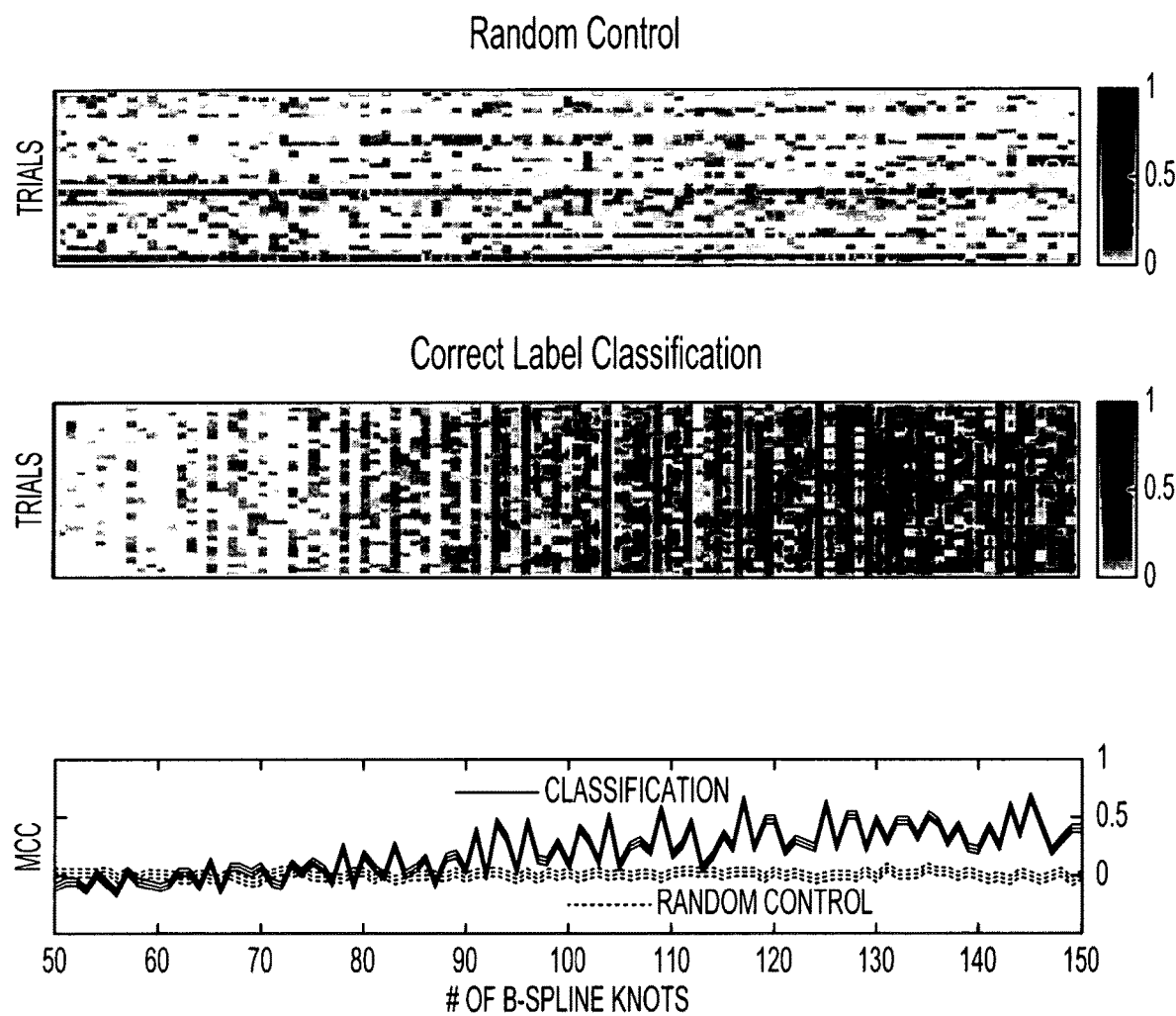
FIG. 20 illustrates a Multi-resolution Multi-Trial Model (MRMT) estimation of a classification model for decoding a memory label according to an aspect of the invention.

FIG. 20 illustrates a Multi-resolution Multi-Trial Model (MRMT) estimation of a classification model for decoding a memory label according to an aspect of the invention. The label to be classified is "Animal". The top two panels show MCCs of all classification models with different temporal resolutions (represented as # of B-spline knot; 50-150) in different cross-validation/estimation trials (1-32). The first panel shows results where the memory labels are randomly shuffled, as a negative control. The second panel shows results with correct labels. The bottom panel shows averaged MCCs across different classification trials. The solid blue line is the negative control while the solid red line is the classification with correct labels. Dashed lines represent the standard errors. It is evident that the classification model can predict whether the sample images belong to the "Animal" category based on the hippocampal CA3 and CA1 patterns to a high degree of accuracy (MCC=0.71), when the temporal resolutions are sufficiently high. In addition, the averaged MCCs under control condition (blue line) indicates that the L1-regularized estimation has effectively avoided overfitting since the MCCs do not increase with the number of B-spline knots.

Figure 21:
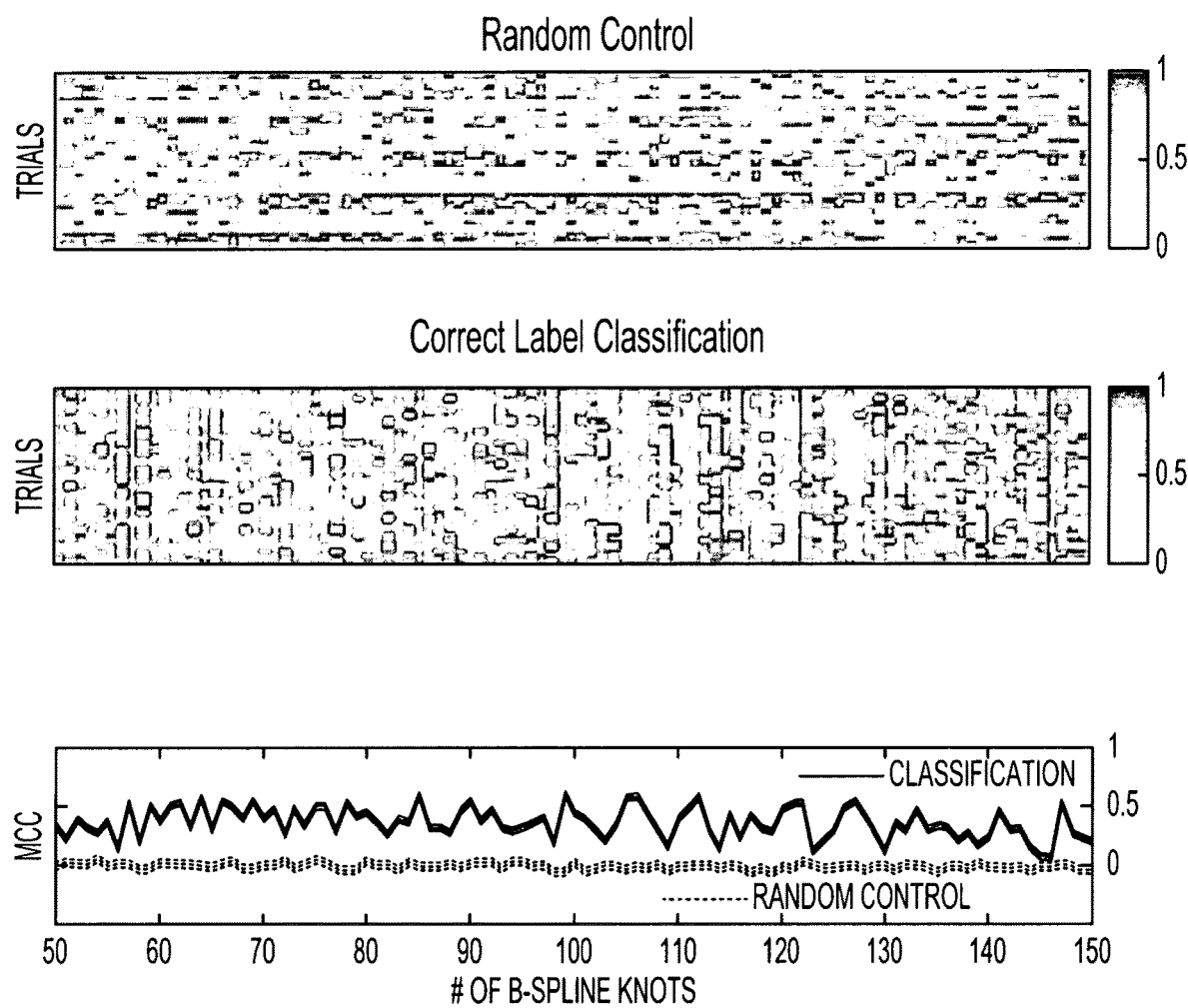
FIG. 21 illustrates a Multi-resolution Multi-Trial Model (MRMT) estimation of a classification model for decoding a memory label according to an aspect of the invention.
Figure 22:
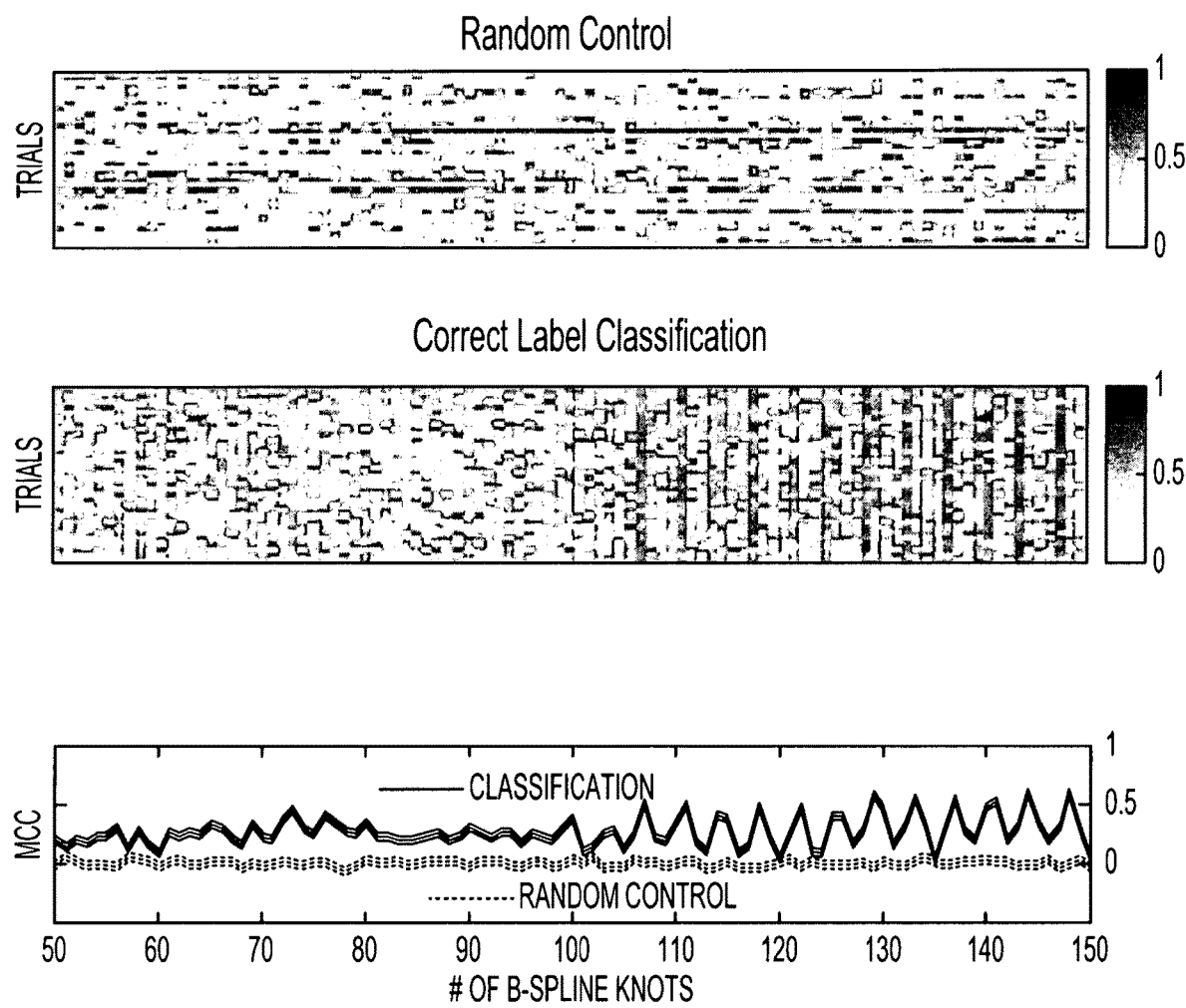
FIG. 22 illustrates a Multi-resolution Multi-Trial Model (MRMT) estimation of a classification model for decoding a memory label according to an aspect of the invention.

FIGS. 21 and 22 illustrate Multi-resolution Multi-Trial Model (MRMT) estimation of a classification model for decoding memory labels according to an aspect of the invention. The labels are "Plant" for FIG. 21 and "Natural" for FIG. 22. In both cases, the MRMT method achieves significant level of classification of the memory categories. FIG. 23 illustrates the MCC's for various labels used for Patient A and Patient B.

Figure 24A:
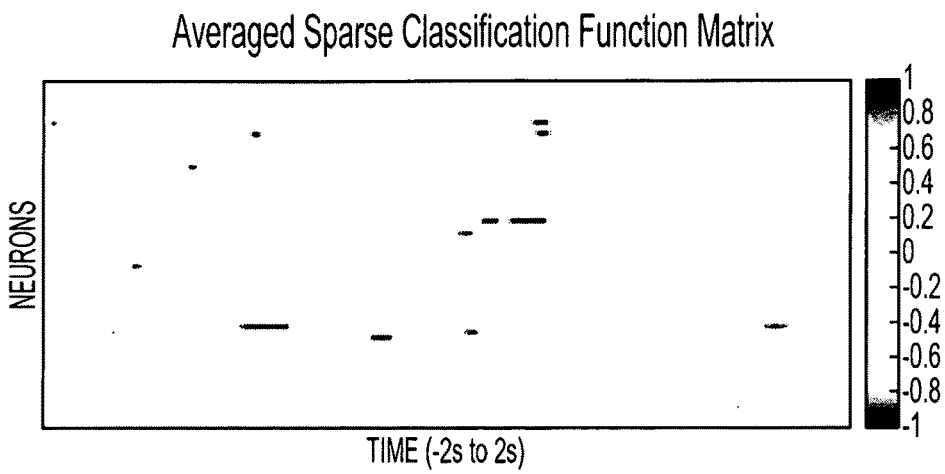
FIGS. 24A-C illustrate averaged calculated Sparse Classification Function Matrices (SCFMs) according to an aspect of the invention.
Figure 24B:
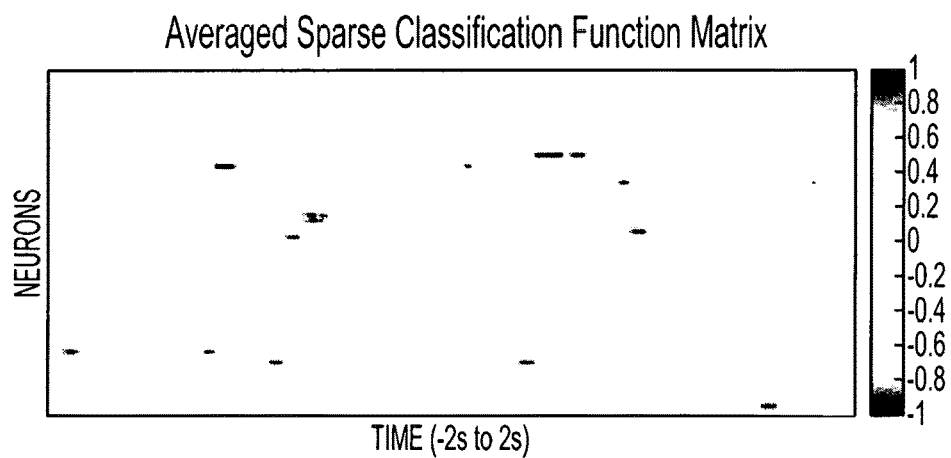
Figure 24C:
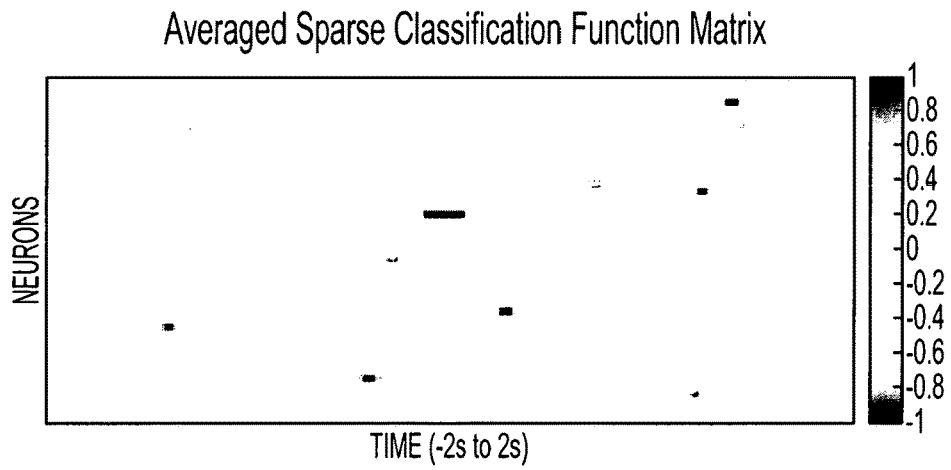

FIGS. 24A-C illustrate averaged calculated Sparse Classification Function Matrices (SCFMs) of "Animal" and "Plant" labels in Patient A, and "Natural" label in Patient B, respectively. In these SCFMs, features used in classification are represented as sparsely distributed spatio-temporal patterns. Positive-value areas (illustrated with warm colors) in SCFMs represent the spatio-temporal regions where spikes are likely to encode a certain memory category or feature (i.e., $\beta=1$), while the negative-value areas (illustrated with cold colors) in SCFMs represent the spatio-temporal regions where spikes are likely to encode memories that do not belong to this memory category or feature (i.e., $\beta=0$).

The features of the embodiments of hippocampal prostheses disclosed herein may be interchanged, substituted, modified, or excluded as desired. The scope of the disclosure is not limited to the hippocampal prostheses disclosed herein, but also extends to the methods of utilizing the hippocampal prostheses.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of systems, apparatuses, and methods as disclosed herein, which is defined solely by the claims. Accordingly, the systems, apparatuses, and methods are not limited to that precisely as shown and described.

Certain embodiments of systems, apparatuses, and methods are described herein, including the best mode known to the inventors for carrying out the same. Of course, variations on these described embodiments will become apparent to those of ordinary skill in the art upon reading the foregoing description. The inventor expects skilled artisans to employ such variations as appropriate, and the inventors intend for the systems, apparatuses, and methods to be practiced otherwise than specifically described herein. Accordingly, the systems, apparatuses, and methods include all modifications and equivalents of the subject matter recited in the claims appended hereto as permitted by applicable law. Moreover, any combination of the above-described embodiments in all possible variations thereof is encompassed by the systems, apparatuses, and methods unless otherwise indicated herein or otherwise clearly contradicted by context.

Groupings of alternative embodiments, elements, or steps of the systems, apparatuses, and methods are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses an approximation that may vary, yet is capable of performing the desired operation or process discussed herein.

The terms "a," "an," "the" and similar referents used in the context of describing the systems, apparatuses, and methods (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the systems, apparatuses, and methods and does not pose a limitation on the scope of the systems, apparatuses, and methods otherwise claimed. No language in the present specification should be construed as indicating any non-claimed element essential to the practice of the systems, apparatuses, and methods.

All patents, patent publications, and other publications referenced and identified in the present specification are individually and expressly incorporated herein by reference in their entirety for the purpose of describing and disclosing, for example, the compositions and methodologies described in such publications that might be used in connection with the systems, apparatuses, and methods. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A hippocampal prosthesis for bypassing a damaged portion of a subject's hippocampus and restoring the subject's ability to form long-term memories, comprising:
   a first set of hippocampal electrodes configured to receive an input signal from at least one of the subject's hippocampus or surrounding cortical region;
   a processing device having:
      a memory, and
      one or more processors operatively coupled to the memory and to the first set of hippocampal electrodes and configured to generate an output signal based on the input signal received from the first set of hippocampal electrodes; and
   a second set of hippocampal electrodes operatively coupled to the one or more processors and configured to receive and transmit the output signal to the subject's hippocampus;
   wherein the output signal is based on a multiple-input multiple-output (MIMO) model of spike train transformation, and wherein the one or more processors are further configured to optimize the MIMO model with a sparse representation of model coefficients.

2. A hippocampal prosthesis for bypassing a damaged portion of a subject's hippocampus and restoring the subject's ability to form long-term memories, comprising:
   a first set of hippocampal electrodes configured to receive an input signal from at least one of the subject's hippocampus or surrounding cortical region;
   a processing device having:
      a memory, and
      one or more processors operatively coupled to the memory and to the first set of hippocampal electrodes and configured to generate an output signal based on the input signal received from the first set of hippocampal electrodes; and
   a second set of hippocampal electrodes operatively coupled to the one or more processors and configured to receive and transmit the output signal to the subject's hippocampus;
   wherein the output signal is based on a multiple-input multiple-output (MIMO) model of spike train transformation, wherein the MIMO model is large-scale and the one or more processors are further configured to estimate the MIMO model using group-lasso estimation.

3. The hippocampal prosthesis of claim 2, wherein the one or more processors are further configured to implement the group-lasso estimation with a local coordinate descent (LCD) technique.

4. A method for bypassing a damaged portion of a subject's hippocampus and restoring the subject's ability to form long-term memories, comprising:
   receiving, by one or more processors, an input signal from a first set of hippocampal electrodes implanted in at least one of the subject's hippocampus or surrounding cortical region;
   generating, by the one or more processors, an output signal based on the input signal received from the first set of hippocampal electrodes, wherein generating the output signal is based on a multiple-input, multiple-output (MIMO) model of spike train transformation;
   optimizing the MIMO model with a sparse representation of model coefficients; and
   outputting, by the one or more processors, the output signal to a second set of hippocampal electrodes in electrical communication with the subject's hippocampus.

5. A method for bypassing a damaged portion of a subject's hippocampus and restoring the subject's ability to form long-term memories, comprising:
   receiving, by one or more processors, an input signal from a first set of hippocampal electrodes implanted in at least one of the subject's hippocampus or surrounding cortical region;
   generating, by the one or more processors, an output signal based on the input signal received from the first set of hippocampal electrodes, wherein generating the output signal is based on a multiple-input, multiple-output (MIMO) model of spike train transformation, wherein the MIMO model is large-scale and the method further comprises estimating the MIMO model using a group-lasso estimation; and
   outputting, by the one or more processors, the output signal to a second set of hippocampal electrodes in electrical communication with the subject's hippocampus.

6. The method of claim 5, wherein the group-lasso estimation comprises using a local coordinate descent (LCD) technique.

7. A hippocampal prosthesis for bypassing a damaged portion of a subject's hippocampus and restoring the subject's ability to form long-term memories, comprising:
   a first set of hippocampal electrodes configured to receive an input signal from at least one of the subject's hippocampus or surrounding cortical region;
   a processing device having:
      a memory, and
      one or more processors operatively coupled to the memory and to the first set of hippocampal electrodes and configured to generate an output signal based on the input signal received from the first set of hippocampal electrodes; and
   a second set of hippocampal electrodes operatively coupled to the one or more processors and configured to receive and transmit the output signal to the subject's hippocampus;
   wherein the output signal is based on a multiple-input multiple-output (MIMO) model of spike train transformation, wherein the MIMO model is large-scale and the one or more processors are further configured to estimate the MIMO model using group-lasso estimation.

8. The hippocampal prosthesis of claim 7, wherein the one or more processors are further configured to implement the group-lasso estimation with a local coordinate descent (LCD) technique.

9. A method for bypassing a damaged portion of a subject's hippocampus and restoring the subject's ability to form long-term memories, comprising:
- receiving, by one or more processors, an input signal from a first set of hippocampal electrodes implanted in at least one of the subject's hippocampus or surrounding cortical region;
- generating, by the one or more processors, an output signal based on the input signal received from the first set of hippocampal electrodes, wherein generating the output signal is based on a multiple-input, multiple-output (MIMO) model of spike train transformation, wherein the MIMO model is large-scale and the method further comprises estimating the MIMO model using a group-lasso estimation; and
- outputting, by the one or more processors, the output signal to a second set of hippocampal electrodes in electrical communication with the subject's hippocampus.

10. The method of claim 9, wherein the group-lasso estimation comprises using a local coordinate descent (LCD) technique.

* * * * *